United States Patent [19]
Reddy et al.

[11] Patent Number: 5,623,068
[45] Date of Patent: Apr. 22, 1997

[54] SYNTHESIS OF DNA USING SUBSTITUTED PHENYLACETYL-PROTECTED NUCLEOTIDES

[75] Inventors: M. Parameswara Reddy, Brea; Firdous Farooqui, LaHabra; Naeem B. Hanna, Fullerton, all of Calif.

[73] Assignee: Beckman Instruments, Inc., Fullerton, Calif.

[21] Appl. No.: 396,993

[22] Filed: Mar. 1, 1995

Related U.S. Application Data

[63] Continuation-in-part of Ser. No. 207,433, Mar. 7, 1994, abandoned.

[51] Int. Cl.$^6$ .............................. C07H 1/02; C07H 19/10; C07H 19/20; C07H 21/00
[52] U.S. Cl. ...................... 536/25.34; 536/25.3; 536/26.1
[58] Field of Search .............................. 536/26.12, 26.13, 536/26.14, 26.1, 25.34, 25.3

[56] References Cited

U.S. PATENT DOCUMENTS

| | | | |
|---|---|---|---|
| 4,415,732 | 11/1983 | Caruthers et al. | 536/26.5 |
| 4,668,777 | 5/1987 | Caruthers et al. | 536/26.5 |
| 4,959,463 | 9/1990 | Froehler et al. | 536/25.3 |
| 4,980,460 | 12/1990 | Molko et al. | 536/26.71 |
| 5,179,200 | 1/1993 | Molko et al. | 536/26.8 |
| 5,204,456 | 4/1993 | Molko et al. | 536/25.33 |

FOREIGN PATENT DOCUMENTS

| | | |
|---|---|---|
| 0241363 | of 1987 | European Pat. Off. . |
| WO86/07362 | of 1985 | WIPO . |

OTHER PUBLICATIONS

Dineva et al. Chem. Abstracts, vol. 120, No. 299197n, 1994, Bioorganic Med. Chem. Lett. 3(12):2781–2784; 1993.
Waldman et al. Sydlett Chem. Abstracts, vol. 120, No. 324101m, (1994) (1):65–7.
Reese et al. "The Protection of Thymine and Guanine Residues in Oligodeoxyribonucleotide Synthesis" *J. Chem. Soc. Perkin Trans*, 1263–71 (1984).
Schulhof et al., "The Final Deprotection Step In Oligonucleotide Synthesis if Reduced to a Mild and Rapid Ammonia Treatment by Using Labile Base–protecting Groups" *Nucleic Acids Research*, vol. 15, No. 2, 397–416 (1987).
Sinha et al., "Labile Exocyclic Amine Protection of Nucleosides in DNA, RNA and Oligonucleotide Analog Synthesis Facilitating N-deacylation, Minimizing Depurination and Chain Degradation" *Biochimie*, 75:13–23 (1993).
Ti et al., "Transient Protection: Efficient One–Flask Synthesis of Protected Deoxynucleosides", *J.Am.Chem.Soc.*, 104: 1316–1319 (1982).
Vu et al., "Fast Oligonucleotide Deprotection Phosphoramidite Chemistry for DNA Synthesis", *Tetrahedron Letters*, vol. 31, No. 50, 7269–7272 (1990).
Ortigao et al., "Antiesense Effect of Oligodeoxynucleotides with Inverted Terminal Internucleotidic Linkages: A Minimal Modification Protecting against Nucleolytic Degradation" *Antisense Research and Development*, 2:129–146 (1992).

Agrawal et al., "Oligodeoxynucleoside Methylphosphonates: Synthesis and Enzimic Degradation" *Tetrahedron Letters*, vol. 28, No. 31, 3539–3542 (1987).
Beaucage et al., "Advances in the Synthesis of Oligonucleotides by the Phosphoramidite Approach" *Tetrahedron*, vol. 48 No. 12, 2223–2311 (1992).
Frauendorf et al., "Automated Synthesis, Strcutre and Biological Actvity of Backbone–Modified Oligonucleotides, The Antisense Approach", *Studies in Natural Products Chemistry*, vol. 13 257–294 (1993).
Froehler et al., "Synthesis of DNA via deoxynucleoside H–phosphonate intermediates", *Nucleic Acids Research*, vol. 14, No. 13, 5399–5407 (1986).
Iyer et al., "3H–1,2–Benzodithiole–3–one 1,1–Dioxide as an Improved Sulfurizing Reagent in the Solid Phase Synthesis of Oligodeoxyribonucleoside Phosphorothioates" *J. Am. Chem. Soc.*, 112, 1253–1254 (1990).
McBride et al., "Amidine Protecting Groups for Oligonucleotide Synthesis" *J. Am. Chem. Soc.*, vol. 108, 2040–2048 (1986).
Scaringe et al., "Chemical Synthesis of biologically active oligoribonucleotides using β–cyanoethyl protected ribonucleoside phosphoramidites" *Nucleic Acids Research*, vol. 18, No. 18, 5433–5441 (1990).
Kohli et al., "Synthesis of Deoxypolynucleotides—A Novel Protecting Group for Deoxyguanosinte" *Indian J. Chem.*, vol. 18B, 272–273 (1979).
Li et al., "Synthesis and Characterization of Oligodeoxynucleotides Containing $O^6$–Methyl–, $O^6$–Ethyl–, and $O^6$–Isopropylguanine" *Biochemistry*, vol. 28, 5779–5786 (1989).

*Primary Examiner*—Gary L. Kunz
*Attorney, Agent, or Firm*—William H. May; Janis C. Henry

[57] ABSTRACT

Deoxyribonucleotide and ribonucleotide derivatives of the general formula I

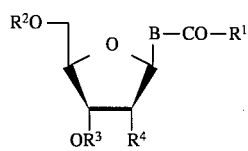

wherein $R^1$ represents —CR'R"—Ar, in which Ar is substituted aryl (as hereinafter defined) and R' and R" are independently selected from the group consisting of hydrogen and lower alkyl; one of —$R^2$ and $R^3$ is a hydroxyl-protecting group and the other is a group suitable for synthesis of polynucleotides or for attachment of the nucleotide to a solid support; $R^4$ is selected from the group consisting of hydrogen, —OH and protected hydroxyl; and B represents a divalent radical corresponding to a purine or pyrimidine base. When synthesis is carried out using these derivatives, the deprotection procedure is reduced to an essentially instantaneous process. The derivatives have acceptable shelf life and are very stable to conventional DNA synthesis conditions. Particularly preferred are those compounds wherein Ar is mono- and dihalo-substituted phenyl.

20 Claims, No Drawings

SYNTHESIS OF DNA USING SUBSTITUTED PHENYLACETYL-PROTECTED NUCLEOTIDES

This is a continuation-in-part of Ser. No. 08/207,433 filed Mar. 7, 1994 now abandoned.

BACKGROUND OF THE INVENTION

The present invention relates generally to the field of chemistry. In particular, the present invention relates to compositions and methods useful in the field of DNA and RNA synthesis.

Current practice in the field of DNA synthesis employs a procedure comprising the following general steps: (a) sequential assembling of T and variously-protected A, C and G nucleotides on an insoluble solid support; (b) cleavage of the synthesized oligonucleotide from the solid support; and (c) deprotection of the oligonucleotide to produce biologically active material. The past decade has witnessed revolutionary improvements in both the coupling chemistry and in automation of the synthesis process. This has made it possible to assemble a typical oligonucleotide sequence (~20 mer) on a solid support in a matter of one hour. However, complete deprotection of the oligonucleotide has heretofore required treatment at 55° C. for 6 hours when T and the conventional and well established nucleotide derivatives—$dA^{bz}$, $dC^{bz}$ and $dG^{ibu}$—are employed. In order to accelerate the deprotection process, the use of protecting groups (for example, phenoxyacetyl groups) which are more labile towards aminolysis by ammonia than those in the conventional nucleotide derivatives has been proposed [Schulhof et al., U.S. Pat. No. 4,980,460; *Nucleic Acids Research* 15:397 (1987)]. Similarly, relatively labile dimethylformamidine protecting groups have been employed [Vu et al., *Tetrahedron Leaders* 31:7269 (1990); McBride et al., *J. Am. Chem. Soc.* 109:2040 (1986)]. Finally, t-butyl phenoxyacetyl groups which are also more labile towards ammonia deprotection have been suggested as an alternative [Sinha et al., *Biochimie* 75:13 (1993)].

While these types of ammonia-labile protecting groups are useful in reducing the deprotection time to between about 15 minutes and 60 minutes at 55° C., their use is associated with significant drawbacks. First, the lability of the protecting groups translates into a significant amount of instability towards DNA synthesis conditions. In addition, phenoxyacetyl protecting groups reduce the solubility of the nucleotide derivatives in solvents typically employed for oligonucleotide synthesis, such as acetonitrile; as a consequence, in order to use nucleotide precursors comprising these groups a mixture of solvents is necessary. Further, problems have been encountered with these materials with respect to their stability, both on the shelf and during DNA or RNA synthesis. Because of these drawbacks, use of these new nucleotide derivatives has not been widespread and there remains a need for improved compositions and methods for use in the synthesis of DNA and RNA.

The use of $N^2$-phenylacetyldeoxyguanosine-5'-phosphate in the synthesis of deoxypolynucleotides has heretofore been proposed [Kohli et al., *Indian J. Chem.* 18B:272 (1979)]. However, it is reported that removal of the N-protecting group in aqueous pyridine required 2 hours at 50° C. with ammonia. Moreover, $N^2$-phenylacetyldeoxy-guanosine-5'-phosphate is not a particularly reactive species in the type of condensation reactions as are conventionally employed in polynucleotide synthesis. Therefore, this compound has not been widely adopted for use in synthesis of polynucleotides.

Similarly, use of the phenylacetyl group for protection of the $NH_2$-group in $O^6$-alkylguanine has been reported [Li et al., *Biochemistry* 28:5779 (1989)]. These compounds were phosphorylated to provide the 2-chlorophenyl phosphates or 2-cyanoethyl phosphates for use in oligonucleotide synthesis by the phosphotriester approach in solution. Deprotection of the $N^2$-group with aqueous ammonia was reported to have a $t_{1/2}$ of at least 48 minutes at 22° C.; the $t_{1/2}$ for the alternate deprotection method proposed (oxime/tetramethylguanidine in aqueous ammonia) was at a minimum 1.8 hours.

It is an object of the present invention to provide novel nucleotide derivatives and methods for the preparation and use thereof.

SUMMARY OF THE INVENTION

Pursuant to the present invention, there is provided a class of deoxyribonucleotide and ribonucleotide derivatives of the general formula I

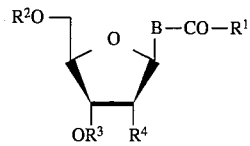

wherein $R^1$ represents —CR'R"—Ar, in which Ar is selected from the group consisting of unsubstituted or substituted aryl (as hereinafter defined) and R' and R" are independently selected from the group consisting of hydrogen and lower alkyl; one of $R^2$ and $R^3$ is a hydroxyl-protecting group and the other is a group suitable for synthesis of polynucleotides or for attachment of the nucleotide to a solid support; $R^4$ is selected from the group consisting of hydrogen, —OH and protected hydroxyl; and B represents a divalent radical corresponding to a purine or pyrimidine base. Preferred as Ar are mono- or dihalo-substituted phenyl (e.g., 4-fluorophenyl, 4-bromophenyl and 3,4-dichlorophenyl). When synthesis is carried out using these derivatives, the deprotection procedure is reduced to an essentially instantaneous process. The new derivatives have acceptable shelf life and are very stable to conventional DNA synthesis conditions. In addition to the convenience provided by the method of the invention, a time saving may also be appreciated when the deprotection process is performed on-line on a DNA synthesizer.

DETAILED DESCRIPTION OF THE INVENTION

The present invention is directed to compounds of the general formula I

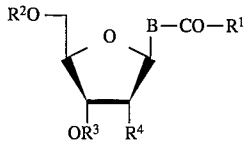

and methods for the preparation and use thereof. In general formula I, $R^1$ represents —CR'R"—Ar, in which Ar is selected from the group consisting of unsubstituted and substituted aryl. For purposes of the present invention, by aryl is meant a monocyclic or polycyclic aromatic group; examples of aryl include, but are not limited to, phenyl, naphthyl, anthracyl, and various aromatic heterocyclic groups, such as pyridinyl, collidinyl, etc. For ease of synthesis, phenyl is presently preferred.

An aryl group for use in accordance with the present invention may be unsubstituted or substituted by one or more non-interfering substituents. A non-interfering substituent is defined for purposes of the present invention as a group which does not react with reagents customarily employed in the synthesis of polynucleotides or attachment of nucleotides to solid supports. Examples of non-interfering substituents include, but are not limited to, the following: lower alkyl (i.e., alkyl of 1 to 5 carbon atoms), lower alkoxy, aryl, aryloxy, $NO_2$, $CN$, $Cl$, $F$, $CO_2R$, $C(O)R$, $SO_2R$, $S(O)R$ and $P(O)(OR)_2$, in which R is alkyl or aryl.

R' and R" are independently selected from the group consisting of hydrogen and lower alkyl (which itself may be substituted by one or more non-interfering groups); it is presently preferred that R' and R" are hydrogen. Particularly preferred are those compounds wherein Ar is mono- or dihalo-substituted phenyl and R' and R" are hydrogen.

In the compounds of formula I, one of $R^2$ and $R^3$ represents a hydroxyl-protecting group. By hydroxyl-protecting group is meant a radical which protects the hydroxyl substituent during the synthesis of polynucleotides or attachment of nucleotides to solid supports, but is readily removed at the end of nucleotide synthesis. For purposes of the present invention, the 4,4'-dimethoxytrityl (DMT) group is particularly preferred. Other suitable groups for protecting the 3'- or 5'-hydroxyl include, but are not limited to, the following: 4,4',4"-tris-(benzyloxy)trityl (TBTr); 4,4',4"-tris-(4,5-dichlorophthalimido)trityl (CPTr); 4,4',4"-tris(levulinyloxy)trityl (TLTr); 3-(imidazolylmethyl)-4,4'-dimethoxytrityl (IDTr); pixyl (9-phenylxanthen-9-yl); 9-(p-methoxyphenyl)xanthen-9-yl (Mox); 4-decyloxytrityl ($C_{10}Tr$); 4-hexadecyloxytrityl ($C_{16}Tr$); 9-(4-octadecyloxyphenyl)xanthene-9-yl ($C_{18}Px$); 1,1-bis-(4-methoxyphenyl)-1'-pyrenyl methyl (BMPM); p-phenylazophenyloxycarbonyl (PAPoc); 9-fluorenylmethoxycarbonyl (Fmoc); 2,4-dinitrophenylethoxycarbonyl (DNPEoc); 4-(methylthiomethoxy)butyryl (MTMB); 2-(methylthiomethoxymethyl)-benzoyl (MTMT); 2-(isopropylthiomethoxymethyl) benzoyl (PTMT); 2-(2,4-dinitrobenzenesulphenyloxymethyl)benzoyl (DNBSB); and levulinyl groups. These and other suitable protecting groups are described in detail in Beaucage & Iyer, *Tetrahedron Letters* 48:2223 (1992), the entire disclosure of which is hereby incorporated by reference.

The other of $R^2$ and $R^3$ in formula I is a group suitable for synthesis of polynucleotides or for attachment of the nucleoside to a solid support. Compounds within the scope of formula I are thus suitable for use both in the initiation of the chain at the solid support and in the propagation of the polynucleotide chain.

In order to facilitate condensation during the synthesis process, it has generally been found appropriate to employ a group at the 3'-hydroxyl or 5'-hydroxyl which is suitably labile in a condensation reaction and forms an appropriate bond with the next nucleotide in the chain. One type of group which has been found particularly useful in this regard is the phosphoramidite group, which is employed in an approach generally referred to in the art as the phosphoramidite method. Examples of suitable phosphoramidite groups include those disclosed in Caruthers et al. U.S. Pat. Nos. 4,415,732 and 4,668,777, the entire disclosures of which are hereby incorporated by reference. Suitable phosphoramidite groups have the general formula

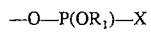

wherein $R_1$ is a hydrocarbyl radical containing up to about 10 carbon atoms which is unsubstituted or substituted by one or more non-interfering substituents and X is $NR_2R_3$, wherein $R_2$ and $R_3$ when taken separately each represent alkyl, aryl, aralkyl, cycloalkyl and cycloalkylalkyl containing up to 10 carbon atoms, $R_2$ and $R_3$ when taken together form an alkylene chain containing up to 5 carbon atoms in the principal chain and a total of up to 10 carbon atoms with both terminal valence bonds of said chain being attached to the nitrogen atom to which $R_2$ and $R_3$ are attached, or $R_2$ and $R_3$ when taken together with the nitrogen atom to which they are attached form a saturated nitrogen heterocycle including at least one additional heteroatom selected from the group consisting of nitrogen, oxygen and sulfur. A variety of exemplary phosphoramidite groups are disclosed in, e.g., Beaucage & Iyer, supra. A phosphoramidite group which is presently preferred for use in accordance with the invention is the (N,N-diisopropyl)-β-cyanoethylphosphoramidite group.

Another type of group suitable for use in accordance with the present invention is the phosphonate group. One phosphonate group of particular interest is the H-phosphonate group of the formula

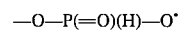

as disclosed in U.S. Pat. No. 4,959,463 to Froehler et al. and Froehler, B. C. et al., *Nucleic Acids Research* 14:5399 (1986), the entire disclosures of which are hereby incorporated by reference. Another type of phosphonate which has received considerable attention is the methyl phosphonate group of the formula

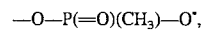

which has particular utility in the synthesis of antisense oligonucleotides. Of course, those skilled in the art would immediately appreciate that groups other than phosphoramidite and phosphonate may alternatively be employed in accordance with the present invention in place of a conventional phosphotriester group; such groups include those containing sulfur (e.g., phosphorothioate and phosphorodithioate) and silicon. Nonetheless, it is presently preferred that a phosphoramidite or phosphonate group be used.

For purposes of attaching the nucleoside to particular types of solid supports, a variety of linking groups may be employed. Selection of a suitable linking group depends upon the particular solid support to which the nucleoside is to be attached. Numerous supports are available for solid-phase synthesis of oligonucleotides, including gel resins of polystyrene and polyacryloylmorpholide, composite supports of polydimethylacrylamide and Kieselguhr, porous inert inorganic materials (such as silica and controlled pore glass) and cellulose paper. For attachment to solid supports containing free amino groups, such as long chain alkylamine controlled pore glass (LCAA-CPG) supports, a succinate group is presently preferred, although other groups (such as, for example, oxalyl) may also be employed.

In general formula I, $R^4$ is selected from the group consisting of hydrogen, —OH and protected hydroxyl. Suitable groups for protecting the hydroxyl in the 2'-position include, but are not limited to, the following: tetrahydropyranyl (Thp); 4-methoxytetrahydropyran-4-yl (Mthp); 1-[(2-chloro-4-methyl)phenyl]-4-methoxypiperidin-4-yl (Ctmp); 1-(2-fluorophenyl)-4-methoxypiperidin-4-yl (Fpmp); 2'-O-[2-(methylthio)phenyl]thiomethyl (MPTM); pixyl and pixyl derivatives, such as 7-chloro-9-(p-anisyl)thioxanthen-9-yl, 7-chloro-9-phenylthioxanthen-9-yl and 9-phenylthioxanthen-9-yl; 2'-O-(o-nitrobenzyl); 1-(2-chloroethoxy)ethyl;

(1-methyl-1-methoxy)ethyl (MME); 2'-O-(4-methoxybenzyl); 2'-O-(3,4-dimethoxybenzyl); 3-methoxy-1,5-dicarbomethoxypentan-3-yl (MDMP); o-nitrobenzenesulfenyl (Nbs); p-nitrophenylethylsulfonyl (NPES); p-cyanophenylethyl (CPES); carbomethoxyethyl-sulfonyl; and t-butyl dimethylsilyl (TBDMS). For purposes of the present invention, the TBDMS group is presently preferred. These and other exemplary protective groups are described in, e.g., Beaucage & Iyer, supra.

B in formula I represents a divalent radical corresponding to a pyrimidine or purine base having at least one exocyclic amino group. Preferred for use in accordance with the present invention are those bases characteristic of guanine, adenine and cytosine; other purine or pyrimidine bases as may be employed in the synthesis of nucleotide analogs may alternatively be used as group B. Preferably, B is selected from the group consisting of

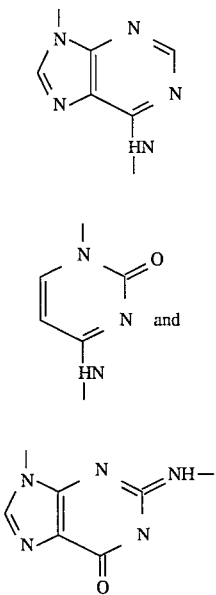

The protective group COR$^1$ is attached to the exocyclic amino group in the compounds of Formula I.

While all of the deoxynucleotide derivatives of the present invention are advantageous in exhibiting stability (both on the shelf and in the synthesis of oligonucleotides), a particular advantage is provided in the use of the deoxyguanosine derivatives of the present invention. As dG determines the rate of the overall deprotection process, the present invention leads to a reduction in deprotection time by providing a suitably labile protecting group for deoxyguanosine. It has been determined that deoxyguanosine derivatives comprising highly labile protecting groups, such as phenoxyacetyl or formamidine, are neither necessary nor appropriate if more nucleophilic deprotection reagents (in particular, methylamine and/or ammonia) are used. Instead, deoxyguanosine derivatives with the only moderately labile protecting groups of the present invention (which additionally better withstand typical DNA synthesis conditions) have been found ideally suitable for use in the synthesis of polynucleotides.

Unlike the labile protecting groups heretofore proposed, the arylacetyl groups employed in accordance with the present invention have been found to be very stable during DNA synthesis. Nonetheless, deprotection of oligonucleotides comprising the compounds of the invention with methylamine/ammonia is substantially complete in about 10–15 minutes at 25° C. (i.e., at room temperature), 1 minute at 37° C. and <30 seconds at 65° C. This constitutes a significant time reduction relative to prior art methods, in which deprotection must be carried out at elevated temperatures (e.g., 65° C.) for extended periods of time (e.g., 3 hours). Particular advantage is achieved with the preferred halo-substituted arylacetyl groups of the present invention; with these preferred groups, essentially complete deprotection of oligonucleotides was effected in 7 minutes at room temperature when methylamine was used, and in 15 minutes at room temperature when methylamine/ammonia was used.

Deprotection of the nucleotides of the present invention is most suitably carried out using compositions as described in application Ser. No. 07/873,915 filed Apr. 24, 1992, now U.S. Pat. No. 5,348,868, commonly assigned to the same assignee as the present invention, the entire disclosure of which is hereby incorporated by reference. As disclosed therein, various combinations of at least one first agent which is at least 5 times more nucleophilic than ammonia, at least one second agent which is at least 1.5 times less polar than water and aqueous ammonia can be effectively utilized as deprotection and cleavage reagents which substantially prevent transamination and side product formation. Preferred embodiments include the following: first agent; first agent and aqueous ammonia; first agent and second agent; and first agent, second agent and aqueous ammonia. Particularly preferred embodiments are methylamine and methylamine/ammonia.

The first agent is suitable a straight chain alkylamine having from between 1 and about 10 carbon atoms. In addition to the nucleophilicity thereof, the length of the alkylamine is also a consideration; preferably, the straight chain alkylamine has from between 1 to about 6 carbon atoms, more preferably from 1 to about 3 carbon atoms, and most preferably 1 carbon atom (i.e., methylamine). Methylamine is particularly preferred, because it is about 40 times less nucleophilic than ammonia. While not wishing to be bound to any particular theory, it is believed that these agents are particularly well suited to attack the bonds between the protecting groups and the individual nucleotides, due to their nucleophilicity and size.

In order to minimize the possibility of transamination (i.e., exchange of amines on a nucleotide, typically manifested as side-product formation), it is preferred in some cases that the deprotection reagent comprise at least one second agent which is less polar than water and acts as a transamination suppression agent. The second agent is preferably selected from the group consisting of straight-chain, branched, cyclic, saturated and unsaturated alkylamines having from between 1 and about 10 carbon atoms and which may further comprise additional functional groups; ethanol; methanol; isopropylamine; acetonitrile; dimethylformamide; tetrahydrofuran; and combinations thereof. Exemplary amines useful as second agents include, but not limited to, the following: t-butylamine, ethylamine, propylamine, isopropylamine, dimethylamine, diethylamine, trimethylamine and secondary butylamine. The preferred second agents have a polarity index value which is at least about 1.5 times less than that for water (which is 10). While not wishing to be bound by any particular theory, it is believed that the second agent substantially reduces or prevents transamination from occurring due to beneficial interactions thereof with nucleotide amines or agents comprising amines involved in a transamination event.

Aqueous ammonia may be added to the deprotection reagent, although this is not a requirement. The presence or absence of aqueous ammonia is largely discretionary. It is believed that the presence or absence of aqueous ammonia does not significantly affect the reagent in terms of the cleavage and deprotection reactions in most instances.

Preferred volume-to-volume ratios of the components of the deprotection reagent are as follows: for reagents comprising a first agent and a second agent, a preferred ratio is between about 9:1 and about 1:9, more preferably from between about 7:3 and about 3:7, and most preferably about 1:1; for reagents comprising a first agent and aqueous ammonia, a preferred ratio is between about 9:1 and about 1:9, more preferably from between about 7:3 and about 3:7, and most preferably about 1:1; and for reagents comprising a first agent, a second agent and aqueous ammonia, a preferred ratio for the three components is from between about 9-1:9-1:9-1 to about 1-9:1-9:1-9, more preferably from about 7-3:7-3:7-3 to about 3-7:3-7:3-7, and most preferably about 1:1:1. As would be readily appreciated by those skilled in the art, deprotection may be effected over a range of temperatures from about room temperature (about 25° C.) to about 100° C., although higher and lower temperatures may in some instances be utilized as long as the integrity of the oligonucleotide is not significantly adversely impacted.

The synthesis of exemplary (4,4'-dimethoxytrityl)-protected deoxyguanosine phosphoramidites within the scope of formula I may be effected as depicted below:

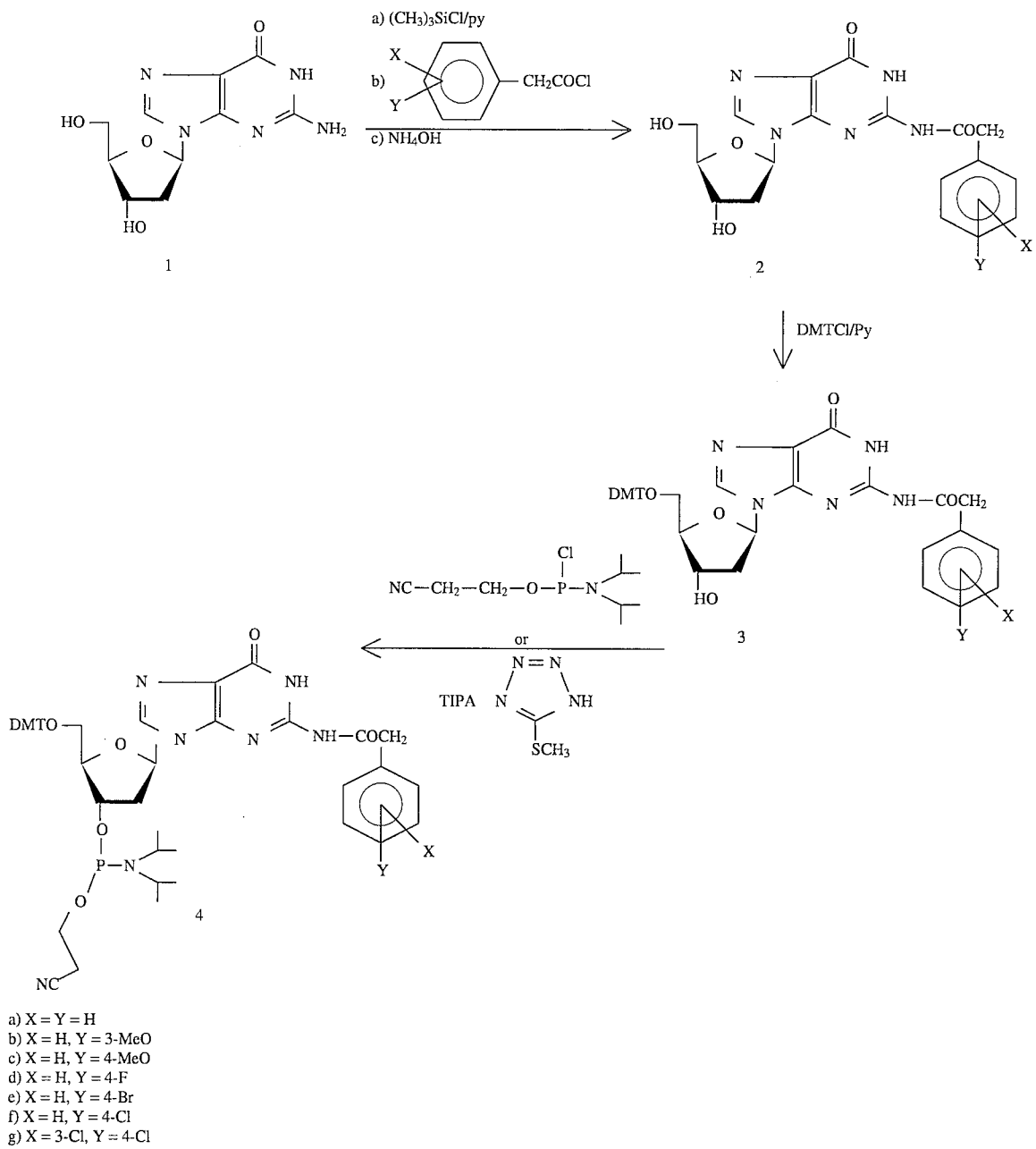

a) X = Y = H
b) X = H, Y = 3-MeO
c) X = H, Y = 4-MeO
d) X = H, Y = 4-F
e) X = H, Y = 4-Br
f) X = H, Y = 4-Cl
g) X = 3-Cl, Y = 4-Cl

In this type of synthetic scheme, the introduction of protective groups other than DMT may of course be carried out in a manner known per se starting from the N²-protected deoxyguanosine 2. Similarly, introduction of an activating group other than the (N,N-diisopropyl)-β-cyanoethylphosphoramidite group or a group suitable for linking to a solid support may be carried out in a manner known per se starting from the 5'-hydroxyl protected deoxyguanosine 3.

Further, in some compounds of the present invention a protective group is introduced at the 5'-hydroxyl group and the reactive group introduced at the 3'-group. Oligonucleotide synthesis has been routinely carried out from the 3' to the 5' terminus in large part because of the ease of synthesis of the monomer units. The 5'-hydroxyl group (a primary hydroxyl group) is significantly more reactive that the 3'-hydroxyl group (a secondary hydroxyl); therefore, it is relatively straightforward to protect the 5'-hydroxyl group with, e.g., DMT and to leave the 3'-hydroxyl free to form, e.g., a phosphoramidite. However, in some situations it is desirable to synthesize oligonucleotides in the opposite sense. For example, using 5'-phosphoramidites for part of the synthesis, it is possible to prepare oligonucleotides containing a hairpin loop in which the strands are parallel. Similarly, preparation of oligonucleotides containing a base at the 3'-terminus which is unsuitable for attachment to a solid support (e.g., 2',3'-ddT and ddI) is most conveniently effected using at least one 5' to 3' synthesis step. Further, protection of antisense oligonucleotides from degradation by intracellular nucleases may be effected by modifying the terminal linkages from the natural 3'–5' linkage to a 3'—3' or 5'—5' linkage. Thus, nucleotide analogs in which the 3'-hydroxyl is protected and the 5'-hydroxyl is primed for further reaction have several significant utilities in the field of oligonucleotide synthesis.

Preparation of compounds of general formula I wherein the 3'-hydroxyl is protected and the 5'-hydroxyl bears a suitable reactive group may be effected in a manner analogous to that described for corresponding nucleotides in Ramalho Ortigao, J. F. et al., *Antisense Research & Development* 2:129 (1992), the entire disclosure of which is hereby incorporated by reference. Briefly, after protection of both the 3'- and 5'-hydroxyls with a suitable protective group (for example, DMT), the 5'-protective group is selectively removed by reaction with $ZnBr_2$ in nitromethane.

The invention may be better understood with reference to the accompanying examples, which are intended for purposes of illustration only and should not be construed as in any sense limiting the scope of the present invention as defined in the claims appended hereto.

EXAMPLE 1

Synthesis of $N^2$-(phenylacetyl)-5'-O-(4,4'-dimethoxytrityl)-2'-deoxyguanosine (3a)

2'-Deoxyguanosine (1)(32.5 g, 120 mmoles) was dried three times by co-evaporation with dried pyridine and suspended in 700 ml of dry pyridine. To this suspension at 0° C. trimethylsilyl chloride (80 ml, 600 mmoles) was added and the mixture stirred at 0° C. for 1 hour. Phenylacetyl chloride (80 ml, 600 mmoles) was added dropwise and the solution stirred for 15 hours. The reaction mixture was then cooled in an ice bath and 150 ml of cold water was added. After 30 minutes, 150 ml of 29% aqueous ammonia was added and the mixture stirred for 30 minutes. The solution was then evaporated to near dryness and the residue dissolved in 700 ml water and 700 ml methylene chloride. The product crystallized out of the aqueous solution upon extraction with $CH_2Cl_2$ was filtered off, washed with $CH_2Cl_2$ (3×70 ml) and ether (3×70 ml) and air dried to yield 27 g (56%) of $N^2$-(phenylacetyl)-2'-deoxyguanosine (2a), as confirmed by spectroscopic and elemental analysis.

$N^2$-(Phenylacetyl)-2'-deoxyguanosine (2a) (23.12 g, 60 mmoles) was dried by coevaporation with dry pyridine (2×100 ml), dissolved in 600 ml of dry pyridine and ice cooled. To this solution, 4,4'-dimethoxytrityl chloride (25.5 g, 72 mmoles) was added. The reaction mixture was stirred at 5° C. for 20 hours. After removing the pyridine under reduced pressure, the resulting residue was taken up in 600 ml of methylene chloride, washed successively with 2×400 ml of 5% $NaHCO_3$ and 1×400 ml of water. The organic layer was dried over anhydrous sodium sulfate and concentrated to near dryness. The product was purified on a silica gel column (6×50 cm) by gradient elution with 1L 0–6% methylene chloride-methanol. The desired fractions were collected, concentrated to about 100 ml and added dropwise to 1.5L cooled hexane (0° C.) to precipitate the product. The precipitated product was filtered, washed with hexane and air dried to yield 24 g (58%) of tritylated product (3a), as confirmed by spectroscopic and elemental analysis.

EXAMPLE 2

Synthesis of $N^2$-(phenylacetyl)-5'-O-(4,4'-dimethoxytrityl)-2'-deoxyguanosine-3'-O-(N,N-diisopropyl)-β-cyanoethyl-phosphoramidite (4a)

Pursuant to a first method, the tritylated product (3a) of Example 1 (4.13 g, 6 mmoles) was dried by successive coevaporations with pyredine, toluene and THF. The dried residue was dissolved in dry THF (35 ml) and N,N,N-diisopropylethylamine (5.2 ml, 24 mmoles) was added, followed by the addition of β-cyanoethylmonochloro-N,N-diisopropylphosphoramidite (3 ml, 12 mmoles) dropwise using a syringe with constant stirring under argon at room temperature over 5 minutes. After 60 minutes of stirring, the reaction mixture was evaporated to dryness. The residue was dissolved in ethyl acetate (200 ml), washed with 10% $NaHCO_3$ solution (2×200 ml) and dried over $Na_2SO_4$. The organic layer was evaporated, the residue was dissolved in ether (50 ml) and added dropwise to hexane (400 ml) at room temperature. The supernatant was decanted and the precipitated product dissolved in ether (70 ml). Hexane (400 ml) was added and the mixture stirred at room temperature for 1 hour. After decanting the supernatant, the product was dissolved in $CH_2Cl_2$ (200 ml). Basic alumina (20 g) was added and stirred at room temperature for 1 hour. The basic alumina was filtered using a sintered glass funnel, the solvent was evaporated and the solid phosphoramidite (4a) (3.6 g, 68% yield) was dried in a desiccator over $P_2O_5$ under reduced pressure.

Pursuant to an alternative method, the tritylated product (9.15 g, 13.32 mmoles) was dried under high vacuum for 5 hours, dissolved in dry methylene chloride (50 ml) and pyridine (1.3 ml) and the resulting solution transferred to an addition funnel. This solution was added dropwise to the stirring mixture of 2-cyanoethyl-N,N,N',N'-tetraisopropylphosphorodiamidite (TIPA) (5.5 ml, 15.99 mmoles) and 5-methylthiotetrazole (1.61 g, 14.65 mmoles) in methylene chloride (20 ml). After 1 hour, the reaction mixture was washed with 7% sodium bicarbonate solution (3×100 ml) and dried over sodium sulfate. The sodium sulfate was filtered in a sintered glass funnel, washed with $CH_2Cl_2$ (2×10 ml) and the solvent evaporated to dryness. The material was dried for 5 hours under high vacuum. The crude material was dissolved in ethyl acetate and transferred to a silica gel column (70–230 mesh, 60Å, preheated at 100°–120° C. overnight) in ethyl acetate. Elution with more ethyl acetate gave the desired material. The material was collected and evaporated to dryness and was put on high vacuum for 5 hours. The residue was repurified on a silica gel column equilibrated with ethyl acetate/diisopropylamine (95/5, v/v) and eluted with ethyl acetate to yield the phosphoramidite (4a) (7.8 g, 66%).

The product was characterized as follows: m.p. 90°–100° C. (dec.); $R_f$=0.5 in $CH_2Cl_2$:MeOH (95:5, v/v); UV (EtOH): λ max 281 nm and 236 nm; IR (KBr): ν 1686 (vs, C=O of amides), 2250 (—C≡N group), 2960 (vs, NH) $cm^{-1}$, $^1$H-NMR ($CDCl_3$); δ 1.16 (m, 12H, 2×CH(C$\underline{H}_3$)$_2$), 2.30 and 2.70 (2 m, 2H, C$_2$, C$\underline{H}_2$), 2.44 and 2.61 (2 t, 2H, —CH$_2$C$\underline{H}_2$CN), 3,27 and 3.76 (m, 14H, C$_5$, C$\underline{H}_2$, 2×C$\underline{H}$(CH$_3$)$_2$, 2×—OC$\underline{H}_3$, C$\underline{H}_2$C$_6$H$_5$, pO C$\underline{H}_2$CH$_2$), 4.25 (m, 1H, C$_4\underline{H}$), 4.61 (m, 1H, C$_3$, $\underline{H}$), 6.19 (t, 1H, J=3.6 Hz, C$_1$, $\underline{H}$), 6.74–7.44 (m, 18H, of C$_6\underline{H}_5$ and aromatic protons of DMTr), and 7.77 (d, 1H, C$_8\underline{H}$); $^{31}$P-NMR (CDCl$_3$): δ 146.96 and 147.65 ppm. Calcd for $C_{48}H_{54}N_7O_8P$•0.5$H_2O$(896.97): C, 64.27; H, 6.18; N, 10.93; P, 3.46. Found: C, 64.38; H, 6.40; N, 10.56; P, 3.15. HPLC retention times of 8.88 min and 10.02 minutes, corresponding to two diastereoisomers (99.57% purity). Conditions: $C_{18}$ Ultrasphere column (Beckman Instruments), 5μ particles, 4.6 mm×25 cm. Bottle A: 0.1M Ammonium Acetate (pH 6.9); Bottle B: Acetonitrile. Program: Flow rate 1 ml/min, 0–20 min at 80% B.

EXAMPLE 3

Synthesis of $N^2$-(3-methoxyphenylacetyl)-5'-O-(4, 4'-dimethoxytrityl)-2'-deoxyguanosine (3b)

To dry 2'-deoxyguanosine (1) (14.2 g, 50 mmoles) in 300 ml of dry pyridine at 0° C. was added trimethylsilyl chloride (33 ml, 250 mmoles) and the mixture stirred at 0° C. for 1 hour. 3-Methoxyphenylacetyl chloride (40 ml, 250 mmoles) was added and the solution maintained at room temperature for 15 hours. The reaction mixture was then cooled in an ice bath and 50 ml of cold water was added. After 30 minutes, 50 ml of 29% aqueous ammonia was added and the mixture stirred for 30 minutes. The solution was then evaporated to near dryness and the residue dissolved in 400 ml water and 400 ml methylene chloride in a separating funnel. The product crystallized out of the aqueous solution upon extraction with CH$_2$Cl$_2$ was filtered off, washed with CH$_2$Cl$_2$ (3×50 ml) and ether (3×50 ml) and air dried to yield 15.56 g (75%) of $N^2$-(3-methoxyphenylacetyl)-2'-deoxyguanosine (2b), as confirmed by spectroscopic and elemental analysis.

$N^2$-(3-Methoxyphenylacetyl)-2'-deoxyguanosine (2b) (2.08 g, 5 mmoles) was dried by coevaporation with dry pyridine (2×30 ml), dissolved in 40 ml of dry pyridine and ice cooled. To this solution, 4,4'-dimethoxytrityl chloride (2.2 g, 6.5 mmoles) was added. The reaction mixture was stirred at 5° C. for 20 hours. After removing the pyridine under reduced pressure, the resulting residue was taken up in 150 ml of methylene chloride and washed successively with 2×100 ml of 5% NaHCO$_3$ and 1×100 ml of water. The organic layer was dried over anhydrous sodium sulfate and concentrated to near dryness. The product was purified on a silica gel column (2×40 cm) by gradient elution with 200 ml 0–6% methylene chloride-methanol. The desired fractions were collected, concentrated to about 30 ml and added dropwise to 200 ml cooled hexane (0° C.) to precipitate the product. The precipitated product was filtered, washed with hexane and air dried to yield 1.7 g (47%) of tritylated product (3b), as confirmed by spectroscopic and elemental analysis.

Following an analogous procedure, the corresponding 3,4-dimethoxyphenylacetyl compound was prepared in a 36% yield and characterized by elemental and spectroscopic analysis.

EXAMPLE 4

Synthesis of $N^2$-(3-methoxyphenylacetyl)-5'-O-(4, 4'-dimethoxytrityl)-2'-deoxyguanosine-3'-O-(N, N-diisopropyl)-β-cyanoethyl-phosphoramidite (4b)

The tritylated nucleoside (3b) prepared as per Example 3 (3.13 g, 4.36 mmoles) was dried under high vacuum for 5 h, dissolved in dry methylene chloride (15 ml) and pyridine (0.6 ml) and the resulting solution was transferred to an addition funnel. This solution was added dropwise to the stirring mixture of 2-cyanoethyl-N,N,N',N'-tetraisopropylphosphorodiamidite (2 ml, 5.87 mmoles) and 5-methylthiotetrazole (0.7 g, 4.6 mmoles) in methylene chloride (10 ml). After 1 hour, the reaction mixture was washed with 7% sodium bicarbonate solution (3×20 ml), and dried over sodium sulfate. The sodium sulfate was filtered in a sintered glass funnel, washed with CH$_2$Cl$_2$ (2×10 ml) and the solvent evaporated to dryness. The material was dried for 5 hours under high vacuum. The crude material was dissolved in ethyl acetate and transferred to silica gel column (70–230 mesh, 60Å, preheated at 100°–120°, overnight) in ethyl acetate. Elution with more ethyl acetate gave the desired material. The material was collected and evaporated to dryness and was put on high vacuum for 5 hours. The residue was repurified on a silica gel column equilibrated with ethyl acetate/diisopropylamine (95/5, v/v), and was eluted with ethyl acetate to yield 3.63 g of the phosphoramidite (4b) (91% yield).

The product was characterized as follows: m.p. 88°–98° C. (dec.); $R_f$=0.6 in CH$_2$Cl$_2$:MeOH (95:5, v/v); UV (EtOH): λ max 281 nm and 235 nm; IR (KBr): ν 1680 (vs, C=O of amides), 1715 (s, C=O of ring amide), 2250 (—C≡N group), 2960 (vs, NH) $cm^{-1}$; $^1$H-NMR(CDCl$_3$): δ 1.16 (m, 12H, 2CH(C$\underline{H}_3$)$_2$), 2.32 and 2.67 (2 m, 2H, C$_2$, C$\underline{H}_2$), 2.44 and 2.61 (2t, 2H,—CH$_2$C$\underline{H}_2$CN), 3.27 and 3.81 (m, 17H, C$_5$, C$\underline{H}_2$, 2×C$\underline{H}$ (CH$_3$)$_2$, 2×—OCH$_3$, C$\underline{H}_2$C$_6$H$_4$—OCH$_3$, pO C$\underline{H}_2$CH$_2$), 4.24 (m, 1H, C$_4$, $\underline{H}$), 4.75 (m, 1H, C$_3$, $\underline{H}$), 6.18 (dt, 1H, J$_{1',2'}$=5.2 Hz, C$_1$, $\underline{H}$), 6.74–7.43 (m, 17H, C$_6$H$_4$ and aromatic protons of DMT), and 7.75 (d, 1H, C$_8\underline{H}$); $^{31}$P-NMR (CDCl$_3$): δ 147.02 and 147.65 ppm. Calcd for $C_{49}H_{56}N_7O_9P$ (918): C, 64.11; H, 6.15; N, 10.68; P, 3.38. Found: C, 63.49; H, 6.34; N, 10.47; P, 3.18. HPLC: Retention times 8.51 min and 9.62 min, corresponding to two diastereoisomers (97.955% purity). Conditions: C$_{18}$ Ultrasphere column (Beckman Instruments), 5μ particles, 4.6 mm×25 cm. Bottle A: 0.1M Ammonium Acetate pH 6.9; Bottle B: Acetonitrile. Program: Flow rate 1 ml/min, 0–20 min at 80% B.

EXAMPLE 5

Synthesis of 5'-O-(4,4'-dimethoxytrityl)-$N^2$-(phenylacetyl)-2'-deoxyguanosine-3'-succinate (DMT-dG$^{PA}$-3'-Succinate)

DMT-dG$^{PA}$ (3a) prepared as in Example 1 (1.72 g, 2.5 mmoles), succinic anhydride (0.755 g, 7.5 mmoles), and DMAP (0.153 g, 1.25 mmoles) were dissolved in dry pyridine (15 ml) and stirred at room temperature for 24 hours. The pyridine was evaporated off and the residue was coevaporated with dry toluene (3×25 ml). The gummy residue was dissolved in CH$_2$Cl$_2$ (100 ml) and washed successively with saturated NaCl solution (3×70 ml) and water (1×70 ml). The CH$_2$Cl$_2$ solution was dried over anhydrous Na$_2$SO$_4$ and was evaporated. The residue was dissolved in CH$_2$Cl$_2$ (20 ml) and was precipitated at room temperature into rapidly stirred hexane (300 ml). The product was filtered and dried under vacuum to yield 1.85 g (94%) of DMT-dG$^{PA}$-3'-Succinate.

The product was characterized as follows: m.p. 160°–170° C. (dec.); UV (EtOH): δ max 281 nm and 236 nm; IR (KBr): ν 1680 (vs, C=O of amides), 1750 (w, C=O of acid), 2800–3600 (NH, OH) cm$^{-1}$, $^1$H-NMR(CDCl$_3$): δ 2.68 (m, 8H, C$_{2'}$ C$\underline{H}_2$, C$\underline{H}_2$C$\underline{H}_2$, C$_{5'}$ C$\underline{H}_2$), 3.31 (s, 2H, C$\underline{H}_2$C$_6$H$_5$), 3.62 (s, 6H, 2×OC$\underline{H}_3$), 4.23 (m, 1H, C$_{4'}$ $\underline{H}$), 5.27 (m, 1H, C$_{3'}$ $\underline{H}$), 6.01 (m, 1H, C$_{1'}$ $\underline{H}$), 6.67–7.29 (m, 18H, DMT group and phenyl group) and 62.69; H, 7.92 (d, 1H, C$_8$ $\underline{H}$). Anal: Calcd for C$_{43}$H$_{41}$N$_5$O$_{10}$•2H$_2$O (823.8): C, 62.69; H 5.46; N, 8.50. Found: C, 62.41; H, 4.87; N, 8.46.

EXAMPLE 6

Synthesis of 5'-O-(4,4'-dimethoxytrityl)-N$^2$-(3-methoxyphenylacetyl)-2'-deoxyguanosine-3'-succinate (DMT-dG$^{MPA}$-3'-Succinate)

DMT-dG$^{MPA}$ (3b) prepared as in Example 3 (0.718 g, 1 mmole), succinic anhydride (0.30 g, 2.5 mmole) and DMAP (0.061 g, 0.42 mmole) were dissolved in dry pyridine (7 ml) and stirred at room temperature for 2 days. The pyridine was evaporated off and the residue was coevaporated with dry toluene (3×10 ml). The gummy residue was dissolved in CH$_2$Cl$_2$ (50 ml) and washed successively with saturated NaCl solution (3×40 ml) and H$_2$O (1×40 ml). The CH$_2$Cl$_2$ solution was dried over anhydrous Na$_2$SO$_4$ and was evaporated. The residue was dissolved in CH$_2$Cl$_2$ (20 ml) and was precipitated at room temperature into rapidly stirred hexane (200 ml). The product was filtered and dried under vacuum to yield 0.72 g (88% yield) of the title compound, DMT dG$^{MPA}$-3'-succinate.

The product was characterized as follows: m.p.: 95°–100° C. (dec.); UV (EtOH): λ max 281 nm and 235 nm; IR (KBr): ν 1680 (vs, C=O of amides), 1750 (s, C=O of acid), 2900–3600 (NH, OH) cm$^{-1}$. $^1$H-NMR (CDCl$_3$): δ 2.60–3.00 (m, 8H, C$_{2'}$ C$\underline{H}_2$, C$\underline{H}_2$C$\underline{H}_2$, C$_{5'}$ C$\underline{H}_2$), 3.73 (s, 2H, C$\underline{H}_2$), 3.79 (2s, 9H, 3×OC$\underline{H}_3$), 4.30 (d, 1H, C$_{4'}$ $\underline{H}$), 5.41 (d, 1H, C$_{3'}$ $\underline{H}$), 6.10 (t, 1H, C$_{1'}$ $\underline{H}$), 6.77–7.39 (m, 17H, DMT group and phenyl group) and 7.76 (d, 1H, C$_8$ $\underline{H}$). Calcd for C$_{44}$H$_{43}$N$_5$O$_{11}$•2H$_2$O (853.82): C, 61.89; H, 5.55; N, 8.20. Found: C, 61.39; H, 5.63; N, 7.93.

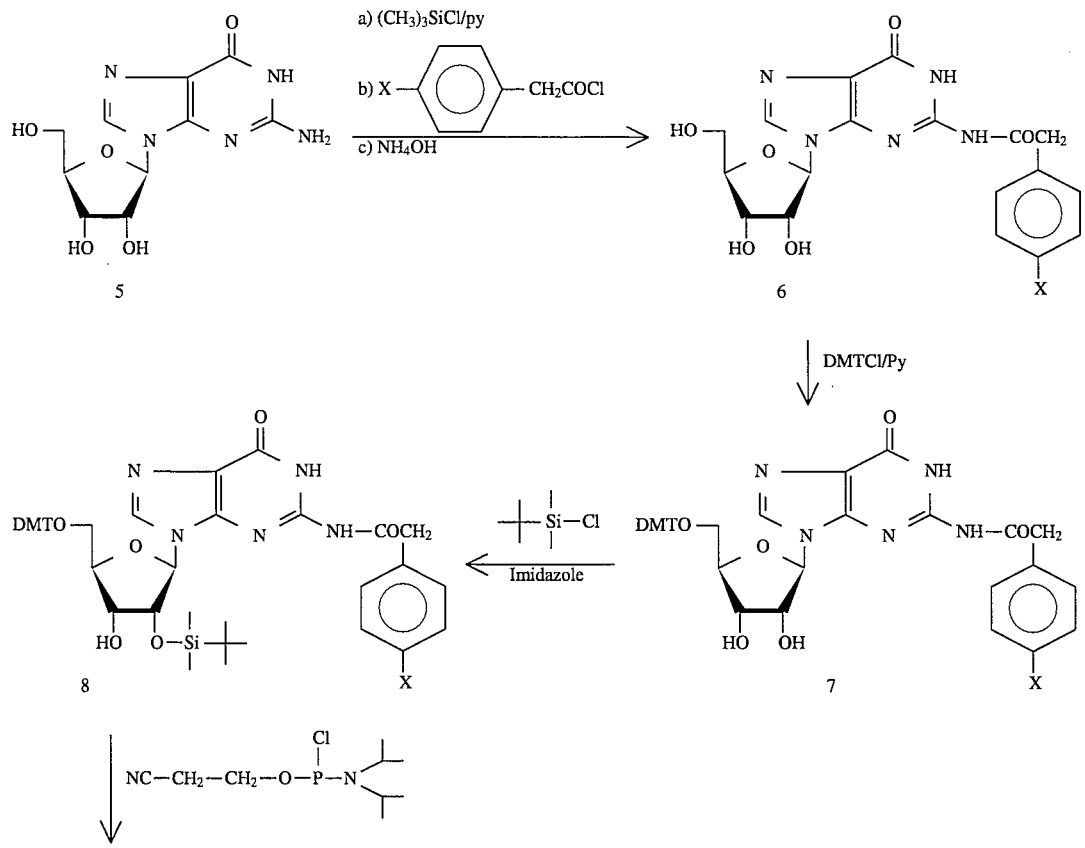

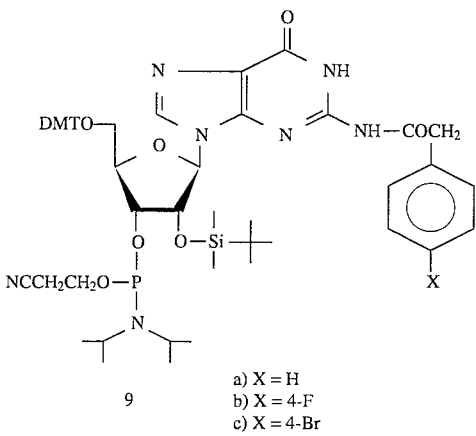

a) X = H
b) X = 4-F
c) X = 4-Br

9

EXAMPLE 7

Synthesis of $N^2$-(phenylacetyl)-guanosine, $rG^{PA}$ (6a)

Guanosine 5 (10.19 g, 36 mmoles) was dried three times by coevaporation with dry pyridine and suspended in 200 ml of dry pyridine. To this was added trimethylsilyl chloride (24 ml, 180 mmoles) at room temperature. After the solution was stirred for 1 hour at room temperature, phenylacetyl chloride (24 ml, 180 mmoles) was added dropwise and the solution was maintained at room temperature with mechanical stirring for 15 hours. The reaction mixture was cooled in an ice bath, and 75 ml of cold water added. After 30 minutes, 75 ml of 29% aqueous ammonia was added and the reaction mixture was stirred for 30 minutes. The solution was then evaporated to near dryness, and the residue was dissolved in 300 ml water and 300 ml methylene chloride. The product crystallizing out of the aqueous solution upon extraction with $CH_2Cl_2$ was filtered off, washed with $CH_2Cl_2$ (3×70 ml) and ether (3×70 ml) and air dried to yield 8.5 g (59% yield) of Ribo $G^{PA}$ 6. The product was characterized as follows: m.p. 160°–170° C. (dec.); UV (EtOH): λ max 280 nm and 258 nm; IR (KBr): ν 1680 (vs, C=O of amide), 1722 (s, C=O of amide ring), and 3000–3500 (NHOH) $cm^{-1}$; $^1$H-NMR (DMSO-$d_6$): δ 3.53 and 3.57 (2m, 2H, $C_5$, $CH_2$), 3.81 (s, 2H, $C_6H_5CH_2$), 3.91 (d, 1H, $C_4$, H), 4.13 (m, 1H, $C_3$, H), 4.42 (d, 1H, $C_2$, H), 5.08 (br, s, 1H, $C_5$, OH), 5.21 (br, s, 1H, $C_3$, OH), 5.81 (d, 1H, $J_{1',2}$=5.64 Hz, $C_1$, H), 7.26–7.41 (m, 5H, $C_6H_5$), 8.28 (s, 1H, $C_8$ H), 11.99 and 12.01 (2s, 2H, 2×NHCO). Calcd for $C_{18}H_{19}N_5O_6$ (401.37): C, 53.86; H, 4.77; N, 17.45. Found: C, 53.49; H, 5.11; N, 17.36

EXAMPLE 8

Synthesis of $N^2$-(4-fluorophenylacetyl)-guanosine, $rG^{FPA}$ (6b)

Guanosine 5 (7.08 g, 25 mmoles) was dried three times by coevaporation with dried pyridine and suspended in 140 ml of dry pyridine. To this was added trimethylsilyl chloride (24 ml, 180 mmoles) at room temperature. After the solution was stirred for 1 hour at room temperature, 4-fluorophenylacetyl chloride (13.9 g, 80 mmoles) was added dropwise and the solution stirred for 15 hours. The reaction mixture was then cooled in an ice bath and 20 ml of cold water was added. After 30 minutes 20 ml of 29% aqueous ammonia was added and the mixture stirred for 30 minutes. The solution was then evaporated to near dryness and the residue dissolved in 300 ml water and 300 ml methylene chloride. The product crystallized out of the solution upon extraction with $CH_2Cl_2$ was filtered off, washed with $CH_2Cl_2$ (3×70 ml) and ether (5×70 ml) and air dried to yield 6 g (57%) of Ribo $G^{FPA}$ 6b. The product was characterized as following: m.p. 160°–170° C. (dec.); UV (EtOH): λ max 280 nm and 258 nm; IR (KBr): ν 1687 (vs, br, C=O of amides), 3000–3500 (NH, OH) $cm^{-1}$. $^1$H-NMR (DMSO-$d_6$): δ 3.36 (m, 2H, $C_5$, $CH_2$), 3.79 (s, 2H, $CH_2C_6H_4$), 3.91(m, 1H, $C_4$, H), 4.13 (m, 1H, $C_3$, H), 4.42(m, 1H, $C_2$, H), 5.81 (t, 1H, $J_{1',2}$=5.64 Hz, $C_1$, H), 7.15–7.37 (m, 4H, $C_6H_4$), 8.27 (d, 1H, $C_8H$), 11.91 and 11.97 (2s, 2H, 2×NHCO).

EXAMPLE 9

Synthesis of $N^2$-(4-bromophenylacetyl)-guanosine, $rG^{BPA}$ (6c)

Guanosine 5 (14.16 g, 50 mmoles) was dried three times by coevaporation with dried pyridine and suspended in 250 ml of dry pyridine. To this was added trimethylsilyl chloride (48 ml, 360 mmoles) at room temperature. After the solution was stirred for 1 hour at room temperature, 4-bromophenylacetyl chloride (35 g, 150 mmoles) was added dropwise and the solution stirred for 15 hours. The reaction mixture was then cooled in an ice bath and 75 ml of cold water was added. After 30 minutes 20 ml of 29% aqueous ammonia was added and the mixture stirred for 30 minutes. The solution was then evaporated to near dryness and the residue dissolved in 500 ml water and 500 ml methylene chloride. The product crystalized out of the solution upon extraction with $CH_2Cl_2$ was filtered off, washed with $CH_2Cl_2$ (3×70 ml) and ether (3×70 ml) and air dried to yield 14.4 g (60%) of Ribo $G^{BPA}$ 6c. The product was characterized as following: m.p. 160°–170° C. (dec.); UV (EtOH): λ max 280 nm and 258 nm; IR (KBr): ν 1688 (vs, br, C=O of amides), 3000–3500 (NH, OH) $cm^{-1}$. $^1$H-NMR (DMSO-$d_6$): δ 3.52 (m, 2H, $C_5$, $CH_2$), 3.67 (s, 2H, $CH_2C_6H_4$), 3.91(m, 1H, $C_4$, H), 4.14 (m, 1H, $C_3$, H), 4.45(m, 1H, $C_2$, H), 5.81 (t, 1H, $J_{1',2}$=5.64 Hz, $C_1$, H), 7.15–7.56 (m, 4H, $C_6H_4$), 8.29 (d, 1H, $C_8H$), 11.92 and 12.04 (2s, 2H, 2×NHCO).

EXAMPLE 10

Synthesis of 5'-O-(4,4'-dimethoxytrityl)-$N^2$-(phenylacetyl)-guanosine, DMT-$rG^{PA}$ (7a)

$N^2$-(Phenylacetyl)-guanosine 6a (8.02 g, 20 mmoles) was dried by coevaporation with dry pyridine (2×60 ml), dissolved in 200 ml of dry pyridine, and 4,4'-dimethoxytrityl chloride (8.17 g, 24 mmoles) was added at room temperature. The reaction mixture was left stirring at room temperature for 20 hours. After removing the pyridine under reduced pressure, the residue was taken up in 400 ml of methylene chloride, washed successively with 2×300 ml of 5% NaHCO$_3$ and 1×300 ml of water. The organic layer was dried over anhydrous sodium sulfate and concentrated to near dryness. The product was purified on a silica gel column (4×50 cm) by gradient elution with 1L 0–6% methylene chloride-methanol. The desired fractions were collected, concentrated to about 50 ml and added dropwise to cooled hexane (0° C., 400 ml) to precipitate the product. The precipitated product was filtered, washed with hexane and air dried to yield 8.73 g of tritylated product 7a (62% yield). The product was characterized as follows: m.p. 150°–155° C. (dec.); R$_f$=0.4 in methylene chloride-methanol (95:5 v/v); UV (EtOH): λ max 281 nm and 236 nm; IR (KBr): λ 1680 (vs, C=O of amide) and 2800–3600 (NH, OH) cm$^{-1}$; $^1$H-NMR (CDCl$_3$): δ 3.21 and 3.41 (2 m, 2H, C$_5$, CH$_2$), 3.69 (2s, 8H, C$_6$H$_5$CH$_2$ and 2×OCH$_3$), 4.08 (br, s, 1H, C$_4$, H), 4.28 (s, 1H, C$_3$, H), 4.45 (m, 1H, C$_2$, H), 5.03 (br, s, 1H, C$_2$, OH), 5.85 (d, 1H, J$_{1',2'}$=6.17 Hz, C$_1$, H), 6.72–7.43 (m, 18H, of C$_6$H$_5$ and aromatic protons of DMTr), 7.63 (s, 1H, C$_8$ H), 9.69 and 9.87 (2b, s, 2H, 2×CONH—). Calcd for C$_{39}$H$_{37}$N$_5$O$_8$ (703.73): C, 66.56; H, 5.30; N, 9.95. Found: C, 66.86; H, 5.80; N, 9.75.

EXAMPLE 11

Synthesis of 5'-O-(4,4'-dimethoxytrityl)-N$^2$-(4-fluorophenylacetyl)-guanosine.DMT-rG$^{FPA}$(7b)

N$^2$-(4-Fluorophenylacetyl)-guanosine 6b (5.03 g, 12 mmoles) was dried by coevaporation with dry pyridine (2×30 ml), dissolved in 80 ml of dry pyridine and 4,4'-dimethoxytrityl chloride (6.10 g, 18 mmloes) was added at room temperature. The reaction mixture was left stirring at room temperature for 20 hours. After removing the pyridine under reduced pressure, the resulting residue was taken up in 300 ml of methylene chloride and washed with 2×300 ml of 5% NaHCO$_3$. The organic layer was dried over anhydrous sodium sulfate and evaporated to near dryness. The product was purified on a silica gel column (4×50 cm) by gradient elution with 1L of 0–6% methylene chloride-methanol. The desired fractions were collected, concentrated to about 50 ml and added dropwise to cold hexane (400 ml, 0° C.) to precipitate the product. The precipitated product was filtered, washed with hexane and air dried to yield 4.47 g (52%) of tritylated product 7. The product was characterized as follows: m.p. 140°–145° C. (dec.); R$_f$=0.45 in CH$_2$Cl$_2$:MeOH (95:5, v/v); UV (EtOH): λ max 280 nm and 236 nm; IR (KBr): ν 1687 (vs, br, C=O of amides), 3000–3500 (NH, OH) cm$^{-1}$. $^1$H-NMR (DMSO-d$_6$): δ 3.34 (m, 2H, C$_5$, CH$_2$), 3.70 (s, 6H, 2×—OCH$_3$), 3.79 (s, 2H, C H$_2$), 4.04 (m, 1H, C$_4$, H), 4.20 (S, 1H, C$_2$, H), 4.53 (m, 1H, C$_2$, H), 5.22 (m, 1H, C$_3$, OH), 5.63 (m, 1H, C$_2$, OH), 5.86 (d, 1H, C$_1$, H), 6.80–7.38 (m, 17H, C$_6$H$_4$ and aromatic protons of DMT), 8.12 (s, 1H, C$_8$H) and 11.94 (br s, 2H, 2×NHCO).

EXAMPLE 12

Sythesis of 5'-O-(4,4'-dimethoxytrityl)-N$^2$-(4-bromophenylacetyl)guanosine.DMT—rG$^{BPA}$(7c)

N$^2$-(4-Bromophenylacetyl)-guanosine 6c (11.15 g, 23.22 mmoles) was dried by coevaporation with dry pyridine (2×60 ml), dissolved in 200 ml of dry pyridine and 4,4'-dimethoxytrityl chloride (9.44 g, 27.86 mmloes) was added at room temperature. The reaction mixture was left stirring at room temperature for 20 hours. After removing the pyridine under reduced pressure, the resulting residue was taken up in 400 ml of methylene chloride and washed with 2×300 ml of 5% NaHCO$_3$. The organic layer was dried over anhydrous sodium sulfate and evaporated to near dryness. The product was purified on a silica gel column (4×50 cm) by gradient elution with 1L of 0–6% methylene chloride-methanol. The desired fractions were collected, concentrated to about 50 ml and added dropwise to cold hexane (400 ml, 0° C.) to precipitate the product. The precipitated product was filtered, washed with hexane and air dried to yield 8.85 g (50%) of tritylated product 7. The product was characterized as follows: m.p. 160°–165° C. (dec.); R$_f$=0.5 in CH$_2$Cl$_2$:MeOH (95:5, v/v); UV (EtOH): λ max 280 nm and 236 nm; IR (KBr): ν 1689 (vs, br, C=O of amides), 2800–3600 (NH, OH) cm$^{-1}$. $^1$H-NMR (DMSO-d$_6$): δ 3.24 (m, 2H, C$_5$, CH$_2$), 3.72 (s, 6H, 2×—OCH$_3$), 3.80 (s, 2H, C H$_2$), 4.05 (m, 1H, C$_4$, H), 4.20 (S, 1H, C$_3$, H), 4.54 (m, 1H, C$_2$, H), 5.21 (m, 1H, C$_3$, OH), 5.63 (m, 1H, C$_2$, OH), 5.87 (d, 1H, J$_{1',2'}$=4.44 Hz, C$_1$, H), 6.80–7.55 (m, 17H, C$_6$H$_4$ and aromatic protons of DMT), 8.13 (s, 1H, C$_8$H), 11.92 and 11.94 (2 br. s, 2H, 2×NHCO).

EXAMPLE 13

Synthesis of 2'-O-(t-butyldimethylsilyl)-5'-O-(4,4'-dimethoxytrityl)-N$^2$-(phenylacetyl)-guanosine [Ribo-DMT-G$^{PA}$-2'-silyl] (8a)

The protected nucleoside 7a from Example 10 (3.5 g, 5 mmoles) was dried by coevaporation with dry pyridine (2×40 ml). It was taken up in 70 ml of pyridine and imidazole (1 g, 14.68 mmoles) was added followed by t-butyldimethylsilyl chloride (1 g, 6.6 mmoles). The reaction mixture was kept under magnetic stirring at room temperature for one day; additional t-BDMS chloride (0.46 g) was then added and the mixture stirred for another day. This process was repeated once. Water (8 ml) was added at 0° C. to the reaction mixture and the solvent evaporated to dryness. The residual yellow gum was taken up in CH$_2$Cl$_2$ (500 ml), washed with saturated aqueous sodium bicarbonate (2×300 ml) and water (300 ml). The organic layer was dried over Na$_2$SO$_4$ and evaporated. The residue was purified by flash column chromatography on silica gel (4×50 cm) by gradient elution with 1L 0–6% methylene chloride-methanol. The desired fractions (those with higher R$_F$ values are the 2'-isomer of silyl product) were collected and evaporated to yield 0.7 g (17% yield) of Ribo-DMT-G$^{PA}$-2'-silyl 8a. The product was characterized as follows: m.p. 150°–160° C. (dec); Rf=0.65 (CH$_2$Cl$_2$: MeOH, 95:5); UV (EtOH): λ max 281 nm and 236 nm; IR (KBr): ν 1687 (vs, br, C=O of amides) and 2950–3650 (NH, OH) cm$^{-1}$; $^1$H-NMR (CDCl$_3$): δ –0.002 (s, 3H, SiCH$_3$), 0.057 (s, 3H, SiCH$_3$), 0.815 (s, 9H, SiC(CH$_3$)$_3$), 3.23 and 3.28 (m, 2H, C$_5$, C H$_2$), 3.50 (2 s, 8H, C$_6$H$_5$CH$_2$ and 2×OCH$_3$) 4.19 (m, 1H, C$_4$, H), 4.29 (m, 1H, C$_3$, H), 4.94 (t, 1H, C$_2$, H), 5.80 (d, 1H, J$_{1',2'}$=6.79 Hz, C$_1$, H), 6.77–7.49 (m, 18H, DMT and C$_6$ H$_5$CH$_2$ groups), 7.81 (s, 1H, C$_8$ H), and 9.14 (br, s, 2H, 2×N HCO); 99.972% purity by HPLC. Calcd for C$_{45}$H$_{51}$N$_5$SiO$_8$ (818): C, 66.07; H, 6.28; N, 8.56; Si, 3.43. Found: C, 66.29; H, 6.67; N, 8.27; Si, 3.84.

EXAMPLE 14

Synthesis of 2'-O-(t-butyldimethylsilyl)-5'-O-(4,4'-dimethoxytrityl)-N$^2$-(4-fluorophenylacetyl)guanosine (Ribo-DMT-G$^{FPA}$-2'-silyl) (8b)

The protected nucleoside 7b from Example 11 (2.53 g, 3.5 mmoles) was dried by coevaporation with dry pyridine (2×30 ml). It was taken up in 50 ml of pyridine and followed by addition of imidazole (0.8 g) and t-butyldimethylsilyl chloride (0.8 g). The reaction mixture was kept under magnetic stirring at room temperature for one day; additional t-BDMSCl (0.6 g) was then added and the mixture stirred at room temperature for another day. Water (6 ml) was added at 0° C. to the reaction mixture and the solvent evaporated to dryness. The residual yellow gum was taken up in $CH_2Cl_2$(100 ml), washed with saturated aqueous sodium bicarbonate (2×100 ml) and water (100 ml). The organic layer was dried over $Na_2SO_4$ and evaporated. The residue was purified by flash column chromatography on a silica gel column (2.5×50 cm) by gradient elution with 200 ml of 0–40% ethyl acetate/dichloromethane. The desired fractions (those containing only the 2'-silylated product with a higher $R_f$ value than the 3'-isomer) were collected and evaporated to yield 0.6 g (17% yield) of Ribo-DMT-$G^{FPA}$-2'-silyl 8b. The product was characterized as follows: m.p. 150°–160° C. (dec.); $R_f$=0.65 in $CH_2Cl_2$:MeOH, 95:5 v/v); UV (EtOH): λ max 280 nm and 236 nm; IR (KBr): ν 1687 (vs, br, C=O of amides), 2950–3650 (NH, OH) $cm^{-1}$. $^1$H-NMR (CDCl$_3$): δ 0.11 (s, 6H, Si(C$\underline{H}_3$)$_2$, 0.87 (s, 9H, SiC(C$\underline{H}_3$)$_3$), 3.35 (m, 2H, C$_5$, C$\underline{H}_2$), 3.38 (s, 6H, 2×—OC$\underline{H}_3$), 3.92 (s, 2H, C$\underline{H}_2$), 4.19 (m, 1H, C$_4$, $\underline{H}$), 4.74 (m, 1H, C$_3$, $\underline{H}$), 5.23 (m, 1H, C$_2$, $\underline{H}$), 6.00 (d, 1H, $J_{1',2'}$=5.70 Hz, C$_1$, $\underline{H}$), 6.94–7.49 (m, 17H, DMT and C$_6\underline{H}_4$ group), 8.24 (s, 1H, C$_8\underline{H}$) and 12.05 (br s, 2H, 2×N$\underline{H}$CO); 99.97% purity by HPLC.

EXAMPLE 15

Synthesis of 2'-O-(t-butyldimethylsilyl)-5'-O-(4,4'-dimethoxytrityl)-N$^2$-(4-bromophenylacetyl)-guanosine (Ribo-DMT-$G^{BPA}$-2'-silyl) (8c)

The protected nucleoside 7c from Example 12 (5.48 g, 3.5 mmoles) was dried by coevaporation with dry pyridine (2×40 ml). It was taken up in 80 ml of pyridine followed by addition of imidazole (1.5 g) and t-butyldimethylsilyl chloride (1.5 g). The reaction mixture was kept under magnetic stirring at room temperature for one day; additional t-BDMSCl (1.3 g) was then added and the mixture stirred for another day. Water (6 ml) was added at 0° C. to the reaction mixture and the solvent evaporated to dryness. The residual yellow gum was taken up in $CH_2Cl_2$(300 ml), washed with saturated aqueous sodium bicarbonate (2×200 ml) and water (200 ml). The organic layer was dried over anhydrous $Na_2SO_4$ and evaporated. The residue was purified by flash column chromatography on a silica gel column (4×50 cm) by gradient elution with 500 ml of 0–40% ethyl acetate/ dichloromethane. The desired fractions (those containing only the 2'-silylated product with a higher $R_f$ value than the 3'-isomer) were collected and evaporated to yield 0.8 g (13% yield) of Ribo-DMT-$G^{BPA}$-2'-silyl 8c. The product was characterized as follows: m.p. 150°–160° C. (dec.); $R_f$=0.65 in $CH_2Cl_2$:MeOH, 95:5 v/v); UV (EtOH): λ max 281 nm and 236 nm; IR (KBr): ν 1687 (vs, br, C=O of amides), 2950–3650 (NH, OH) $cm^{-1}$. $^1$H-NMR (CDCl$_3$): δ 0.12 (s, 6H, Si(C$\underline{H}_3$)$_2$, 0.89 (s, 9H, SiC(C$\underline{H}_3$)$_3$), 3.36 (m, 2H, C$_5$, C$\underline{H}_2$) 3.90 (s, 6H, 2×—OC$\underline{H}_3$), 4.01 (s, 2H, C$\underline{H}_2$), 4.19 (m, 1H, C$_4$, $\underline{H}$), 4.75 (m, 1H, C$_3$, $\underline{H}$), 5.24 (m, 1H, C$_2$, $\underline{H}$), 6.01 (d, 1H, $J_{1',2'}$=5.71 Hz, C$_1$, $\underline{H}$), 6.97–7.50 (m, 17H, DMT and C$_6\underline{H}_4$ group ), 8.25 (s, 1H, C$_8\underline{H}$) and 12.10 (br. s, 2H, 2×N$\underline{H}$CO); 99.90 % purity by HPLC.

EXAMPLE 16

Synthesis of N$^2$-(phenylacetyl)-5'-O-(4,4'-dimethoxytrityl)-2'-O-(t-butyldimethylsilyl)-guanosine-3'-O-(N,N-diisopropyl)-β-cyanoethylphosphoramidite (9a)

The nucleoside 8a of Example 13 (0.61 g, 0.75 mmole) was dried by successive coevaporations with pyridine, toluene and THF. The dried residue was dissolved in dry THF (6 ml) and redistilled N,N,N-diisopropylethylamine (0.7 ml, 3.2 mmoles) was added, followed by the addition of β-cyanoethylmonochloro-N,N-diisopropyl-phosphoramidite (0.65 ml, 2.6 mmoles) dropwise using a syringe with constant stirring under argon at room temperature over 5 minutes. After 60 minutes of stirring, the reaction mixture was diluted with ethyl acetate (50 ml), washed with 10% NaHCO$_3$ solution (2×50 ml) and dried over Na$_2$SO$_4$. The organic layer was evaporated. The crude material was dissolved in ethyl acetate and transferred to silica gel column (70–230 mesh, 60Å, preheated at 100°–120° C., overnight) in ethyl acetate. Elution with more ethyl acetate gave the desired material. The material was collected and evaporated to dryness and was put under high vacuum for 5 hours to yield the phosphoramidite 9a (0.41 g, 50% yield). The product was characterized as follows: m.p. 90°–100° C. (dec.); $R_f$=0.7 in $CH_2Cl_2$: MeOH (95:5, v/v); UV (EtOH): λ max 281 nm and 236 nm; IR (KBr): ν 1686 (vs, C=O of amide ring), 1720 (s, C=O of phenylacetyl), 2256 (—C≡N group) and 2960 (vs. NH) $cm^{-1}$; $^1$H-NMR (CDCl$_3$): δ −0.1 and 0.2 (2s, 6H, 2×SiC$\underline{H}_3$), 1.01 (s, 9H, SiC(C$\underline{H}_3$)$_3$), 1.1–1.51 (m, 12H, 2 CH(C$\underline{H}_3$)$_2$), 2.89–3.08 (m, 2H, C$\underline{H}_2$CN), 3.5–3.71 (m, 6POC$\underline{H}_2$, C$_5$, C$\underline{H}_2$, 2 ×C$\underline{H}$(CH$_3$)$_2$), 3.90 (2s, 8H, C$_6$H$_5$C$\underline{H}_2$ and 2×OC$\underline{H}_3$), 4.3–4.6 (m, 2H, C$_3$, $\underline{H}$ and C$_4$, $\underline{H}$), 5.05 and 5.35 (2m, 1H, C$_2$, $\underline{H}$), 5.93 and 6.16 (2d, 1H, C$_1$, $\underline{H}$), 7.01–7.72 (m, 18H, C$_6\underline{H}_5$ and DMT groups), 8.07 and 8.15 (2s, 1H, C$_8$ $\underline{H}$) and 9.10 (br, s, 1H, N $\underline{H}$CO); $^{31}$P-NMR (CDCl$_3$): 146.5 and 147.9 ppm; HPLC: 96% purity. Calcd for C$_{54}$H$_{68}$N$_7$SiO$_9$P•H$_2$O (1036.29): C, 62.58; H, 6.81; N, 9.46; Si, 2.71; P, 2.99. Found: C, 62.34; H, 7.00; N, 8.91; Si, 2.52; P, 2.85.

EXAMPLE 17

Synthesis of N$^2$-(4-fluorophenylacetyl)-5'-O-(4,4'-dimethoxytrityl)-2'-O-(t-butyldimethylsilyl)-guanosine-3'-O-(N,N-diisopropyl)-β-cyanoethylphosphoramidite (9b)

The nucleoside 8b of Example 14 (0.84 g, 1 mmole) was dried by successive coevaporations with pyridine, toluene and THF. The dried residue was dissolved in dry THF (6 ml) and redistilled N,N-diisopropylethylamine (0.7 ml, 3.2 mmoles) was added, followed by the addition of β-cyanoethylmonochloro-N,N-diisopropyl-phosphoramidite (0.65 ml, 2.6 mmoles) dropwise using a syringe with constant stirring, under argon at room temperature over 5 minutes. After 60 minutes of stirring, the reaction mixture was diluted with ethyl acetate (50 ml), washed with 10% NaHCO$_3$ aqueous solution (2×50 ml) and dried over anhydrous Na$_2$SO$_4$. The solution was concentrated and transferred to a silica gel column (70–230 mesh, 60Å, preheated at 100°–120° C. overnight, packed with ethyl acetate). After elution with more ethyl acetate the desired fractions were collected and evaporated to dryness and further dried in high vacuum for 15 hours to yield the phosphoramidite 9b (0.50 g, 50% yield).

EXAMPLE 18

Synthesis of $N^2$-(4-bromophenylacetyl)-5'-O-(4,4'-dimethoxytrityl)-2'-O-(t-butyldimethylsilyl)-guanosine-3'-O-(N,N-diisopropyl)-β-cyanoethylphosphoramidite (9c)

The nucleoside 8c of Example 15 (0.90 g, 1 mmole) was dried by successive coevaporations with pyridine, toluene and THF. The dried residue was dissolved in dry THF (6 ml) and redistilled N,N,N-diisopropylethylamine (0.7 ml, 3.2 mmoles) was added, followed by the addition of β-cyanoethylmonochloro-N,N-diisopropyl-phosphoramidite (0.65 ml, 2.6 mmoles) dropwise using a syringe with constant stirring, under argon at room temperature over 5 minutes. After 60 minutes of stirring, the reaction mixture was diluted with ethyl acetate (50 ml), washed with 10 % $NaHCO_3$ aqueous solution (2×50 ml) and dried over anhydrous $Na_2SO_4$. The solution was concentrated and transferred to a silica gel column (70–230 mesh, 60Å, preheated at 100°–120° C. overnight, packed with ethyl acetate). After elution with more ethyl acetate the desired fractions were collected and evaporated to dryness and further dried in high vacuum for 15 hours to yield the phosphoramidite 9c (0.55 g, 50% yield).

EXAMPLE 19

Synthesis of $N^2$-(phenylacetyl)-5'-O-(4,4'-dimethoxytrityl)-2'-deoxyguanosine-3'-(N,N-diisopropyl)-methyl phosphonamidite

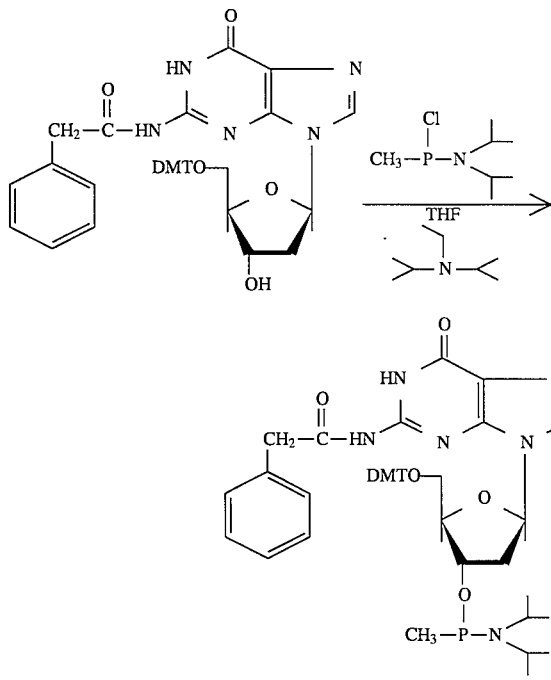

The nucleoside of Example 1 (2.20 g, 3.2 mmoles) was dried by successive coevaporations with pyridine, toluene and THF. The dried residue was dissolved in dry THF (15 ml). Redistilled N,N,N-diisopropylethylamine (2.4 ml, 11.1 mmoles) was added, followed by the addition of methylmonochloro-N,N-diisopropylphosphonamidite (1.6 ml, 6 mmoles) dropwise using a syringe with constant stirring under argon at room temperature over 5 minutes. After 60 minutes of stirring, the reaction mixture was diluted with ethyl acetate (100 ml), washed with 10% $NaHCO_3$ solution (2×100 ml) and dried over $Na_2SO_4$. The crude material was dissolved in ethyl acetate and transferred to a silica gel column (70–230 mesh, 60Å, preheated at 100°–120° C. overnight) in ethyl acetate. Elution with ethyl acetate gave the desired material. The material was collected and evaporated to dryness and was put on high vacuum for 5 hours to yield the phosphonamidite (1.6 g, 60% yield).

The product was characterized as follows: m.p. 100°–110° C. (dec.); $R_f$=0.6 in $CH_2Cl_2$:MeOH (95:5, v/v); UV (EtOH): λ max 281 nm, 276 nm and 235 nm; IR (KBr): v 1687 (vs, C=O of amide ring), 1721 (s, C=O of phenylacetyl), 3000–3100 (NH) $cm^{-1}$. $^1$H-NMR ($CDCl_3$): δ 1.0–1.29 (m, 15H, P—$CH_3$ and $CH_3$ iPr), 2.50 and 2.82 (2m, 2H, $C_{2'}$·$CH_2$), 3.40 and 3.76 (m, 4H, $C_{5'}$·$CH_2$, 2×$CH$ iPr, 3.74 (s, 2H, $CH_2$ $C_6H_5$), 3.76 (s, 6H, 2×$OCH_3$ DMTr), 4.11 (m, 1H, $C_{4'}$·$H$), 4.58 (m, 1H, $C_{3'}$·$H$), 6.12 (m, 1H, $C_{1'}$·$H$), 6.75–7.45 (m, 18H, $C_6H_5$ and aromatic protons of DMTr), 7.78 (s, 1H, $C_8$ $H$), and 11.62 (br, s, 1H, N$H$CO); $^{31}$P-NMR ($CDCl_3$): δ 119.26 and 117.56 ppm. Calcd for $C_{46}H_{33}N_6O_7P$·$H_2O$ (850.9): C, 64.93; H, 6.52; N, 9.88; P, 3.64. Found: C, 65.20; H, 6.81; N, 9.53; P, 3.75. HPLC retention times of 16.69 min and 17.66 minutes, corresponding to two diastereoisomers (99.12% purity). Conditions: $C_{18}$ Ultrasphere column (Beckman Instruments, Catalog No. 235329), 5μ particles, 4.6 mm×25 cm. Bottle A: 0.1M Ammonium Acetate (pH 6.9); Bottle B: Acetonitrile. Program: Flow rate 1 ml/min, 0–20 min at 80% B.

EXAMPLE 20

Synthesis of 5'-O-(dimethoxytrityl)-$N^2$-phenylacetyl-2'-deoxyguanosine-3'-hydrogen phosphonate triethylammonium salt

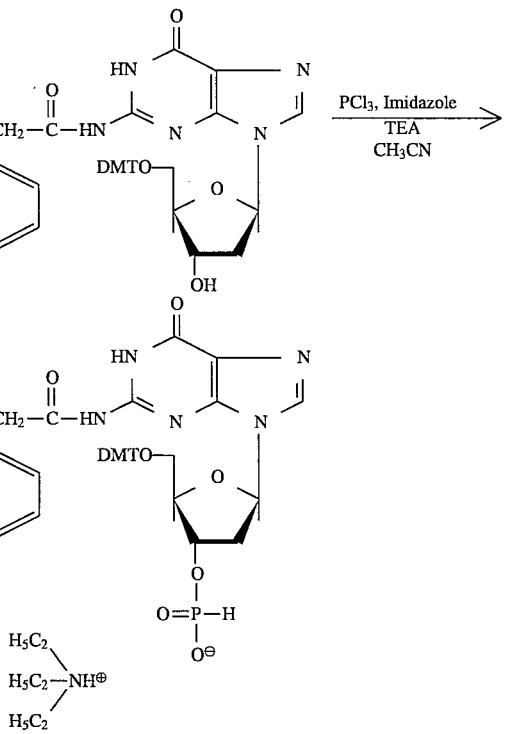

Imidazole (3.6 g, 53 mmoles) was dissolved in acetonitrile (100 ml) and at 0° C., $PCl_3$ (1.4 ml, 16 mmoles) and TEA (7.8 ml) was added. The reaction mixture was stirred for 30 minutes; then DMT dG$^{Pa}$ prepared as in Example 1 (2.55 g, 3.7 mmoles) in acetonitrile (100 ml) was added dropwise over a 30 minute period. The reaction mixture was stirred at room temperature for 4 hours. Water (25 ml) was added and stirring continued for another 30 minutes. The solution was evaporated, then coevaporated twice with 50 ml pyridine/TEA (4:1, v/v). The residue was dissolved in CHCl$_3$ (200 ml), washed with water (200 ml), dried over Na$_2$SO$_4$, filtered and evaporated. The residue after evaporation was dissolved in CHCl$_3$ (10 ml) and precipitated with ether (500 ml). The filtered product was washed with ether and dried to give 2.5 g (79% yield) of the desired product. The product was purified by passing through a silica gel column (1.5×40 cm, 70–230 mesh) and eluted with 200 ml portions of gradient 5–20% MeOH/CHCl$_3$ containing 1% TEA. The pure fractions were collected and evaporated to yield 1.5 g of the desired product.

The product was characterized as follows: m.p. 120°–135° C. (dec.); UV (EtOH): λ max 275 nm and 234 nm. $^1$H-NMR (CDCl$_3$): δ 1.33 (t, 3H, NCH$_2$C$\underline{H}_3$), 2.67 and 3.10 (2 m, 2H, C$_2$·C$\underline{H}$2), 3.05 (q, 2H, NC$\underline{H}_2$CH$_3$), 3.38 (m, 2H, C$_5$·CH$_2$), 3.85 (s, 6H, 2×OCH$_3$), 3.87 (s, 2H, C$\underline{H}_2$C$_6$H$_5$), 4.33 (m, 1H, C$_4$·$\underline{H}$), 5.17 (m, 1H, C$_3$·$\underline{H}$), 6.25 (t, 1H, C$_1$·$\underline{H}$), 6.86 (d, 1H, J$_{P-H}$=555 Hz, $\underline{H}$—P), 6.72–7.40 (m, 18H, DMT aromatic protons and C$_6$H$_5$CH$_2$) and 8.22 (s, 1H, C$_8$$\underline{H}$); $^{31}$P-NMR (CDCl$_3$): δ 4.015 and −1.129 ppm, J$_{H-P}$= 624.9 Hz. HPLC: 100% purity.

EXAMPLE 21

Synthesis of N$^2$-(substituted phenylacetyl)-2'-deoxyguanosine

To 5.7 g (20 mmoles) of 2'-deoxyguanosine (1) dried three times by co-evaporation with dry pyridine and suspended in 120 ml of dry pyridine was added 13.3 ml (100 mmoles) of trimethylsilyl chloride at room temperature. After the solution was stirred 1 hour at room temperature, 3.5 equivalents of substituted phenylacetyl chloride derivative was added dropwise and the solution was stirred at room temperature for 15 hours. The reaction mixture was cooled in an ice bath, and 20 ml of cold water was added. After 30 minutes, 10 ml of 29% aqueous ammonia was added and the reaction mixture was stirred for 30 minutes. The solution was then evaporated to near dryness, and the residue was dissolved in 200 ml of water and 200 ml of methylene chloride. The product that was crystallized out of the aqueous solution upon extraction with CH$_2$Cl$_2$ was filtered off, washed with CH$_2$Cl$_2$ (3×70 ml) and ether (3×70 ml) and dried.

N$^2$-(4-Fluorophenylacetyl)-2'-deoxyguanosine (2d):

Yield: 77%; HPLC purity: 97.284% m.p. 160°–165° C. (dec.) UV (EtOH): λ max 280 nm and 254 nm IR (KBr): ν 1694 (vs, br, C=O of amides), 3000–3500 (—NH, OH) cm$^{-1}$. $^1$H-NMR(DMSO-d): δ 2.29 and 2.55 (2m, 2H, C$_2$, C$\underline{H}_2$), 3.56 (m, 2H, C$_5$, C$\underline{H}_2$), 3.81 (s, 2H, C$\underline{H}_2$), 3.85 (t, 1H, C$_4$·,$\underline{H}$), 4.38 (m, 1H, C$_3$·$\underline{H}$), 4.97 (t, 1H, C$_5$· O$\underline{H}$, exchangeable with D$_2$O), 5.33 (d, 1H, C$_3$· O$\underline{H}$, exchangeable with D$_2$O), 6.22 (t, 1H, J$_{1',2'}$=6.60 Hz, C$_1$·$\underline{H}$), 7.14–7.40 (m, 4H, C$_6$H$_4$), 8.25 (s, 1H, C$_8$$\underline{H}$), 11.90 and 11.97 (2s, 2H, 2×NHCO, exchangeable with D$_2$O).

Analysis: Calcd for C$_{18}$H$_{18}$N$_5$O$_5$F (403.36): C, 53.59; H, 4.90; N, 17.36; F, 4.71. Found: C, 53.60; H, 4.47; N, 17.13; F, 4.63.

N$^2$-(4-bromophenylacetyl)-2'-deoxyguanosine (2e):

Yield: 80%; HPLC purity: 97.207% m.p. 170°–175° C.(dec.) UV (EtOH): λ max 280 nm and 256 nm IR (KBr): ν 1686 (vs, br, C=O of amides), 3000–3500 (—NH, OH) cm$^{-1}$. $^1$H-NMR(DMSO-d$_6$):δ 2.29 and 2.55 (2m, 2H, C$_2$·C$\underline{H}_2$), 3.55 (m, 2H, C$_5$·C$\underline{H}_2$), 3.81 (s, 2H, C$\underline{H}_2$), 3.85 (t, 1H, C$_4$·$\underline{H}$), 4.38 (m, 1H, C$_3$·$\underline{H}$), 4.96 (t, 1H, C$_5$· O$\underline{H}$, exchangeable with D$_2$O), 5.34 (d, 1H, C$_3$· O$\underline{H}$, exchangeable with D$_2$O), 6.22 (t, 1H, J$_{1',2'}$=6.60 Hz, C$_1$$\underline{H}$), 7.30–7.54 (2d, 4H, C$_6$ $\underline{H}_4$), 8.25 (s, 1H, C$_8$$\underline{H}$), 11.89 and 11.97 (2s, 2H, 2×N$\underline{H}$CO, exchangeable with D$_2$O).

Analysis: Calcd for C$_{18}$H$_{18}$N$_5$O$_5$Br (464.28): C, 46.56; H, 3.90; N, 15.09; Br, 17210. Found: C, 46.32; H, 4.10; N, 15.15; Br, 17.35.

N$^2$-(4-Chlorophenylacetyl)-2'-deoxyguanosine (2f):
Yield: 70% m.p. 172°–178° C. (dec.) UV (EtOH): λ max 278 nm and 254 nm IR (KBr): ν 1694 (vs, br, C=0 of amides), 2900–3500 (—NH, OH) cm$^{-1}$. $^1$H-NMR(DMSO-d$_6$): δ 2.31 and 2.55 (2m, 2H, C$_2$· C$\underline{H}_2$), 3.59 (m, 2H, C$_5$· C$\underline{H}_2$), 3.85 (s, 2H, C$\underline{H}_2$), 3.85 (t, 1H, C$_4$·$\underline{H}$), 4.38 (m, 1H, C$_3$·H), 5.30 (d, 1H, C$_3$· O$\underline{H}$, exchangeable with D$_2$O), 6.22 (t, 1H, J$_{1',2'}$=6.99 Hz, C$_1$·$\underline{H}$), 7.40 (m, 4H, C$_6$H$_4$), 8.24 (s, 1H, C$_8$$\underline{H}$), 11.89 and 11.90 (2s, 2H, 2×NHCO, exchangeable with D$_2$O).

Analysis: Calcd for C$_{18}$H$_{18}$N$_5$O$_5$Cl.0.5H$_2$O(428.81): C, 50.41; H, 4.46; N, 16.33; Cl, 8.27. Found: C, 50.51; H, 4.35; N, 16.50; Cl, 8.45

N$^2$-(3,4-dichlorophenylacetyl)-2'-deoxyguanosine (2g):

Yield: 88%. m.p. 210°–220° C. (dec.) UV (EtOH): λ max 282 nm and 254 nm IR (KBr): ν 1694 (vs, br, C=O of amides), 3000–3500 (—NH, OH) cm$^{-1}$. $^1$H-NMR(DMSO-d$_6$): δ 2.25 and 2.60 (2m, 2H, C$_2$· C$\underline{H}_2$), 3.54 (m, 2H, C$_5$· C$\underline{H}_2$), 3.86 (s, 3H, C$\underline{H}_2$ and C$_4$· $\underline{H}$), 4.39 (m, 1H, C$_3$·$\underline{H}$), 5.30 (br, s, 1H, C$_3$· O$\underline{H}$, exchangeable with D$_2$O), 6.22 (t, 1H, J$_{1',2'}$=6.78 Hz, C$_1$·$\underline{H}$), 7.33–7.65 (m, 3H, C$_6$$\underline{H}_3$), 8.28 (s, 1H, C$_8$$\underline{H}$), 11.86 and 11.97 (2s, 2H, 2×N$\underline{H}$CO, exchangeable with D$_2$O).

Analysis: Calcd for C$_{18}$H$_{17}$N$_5$O$_5$Cl$_2$ (454.27): C, 47.59; H, 3.77; N, 15.42; Cl, 15.61. Found: C, 47.08; H, 3.70; N, 15.20; Cl, 16.08

N$^2$-(4-methoxyphenylacetyl)-2'-deoxyguanosine (2c):

Yield: 67% m.p. 131°–140° C. (dec.) UV (EtOH): λ max 280 nm and 258 nm IR (KBr): ν 1690 (vs, br, C=0 of amides), 3000–3500 (—NH, OH) cm$^{-1}$. $^1$H-NMR(DMSO-d$_6$): δ 2.27 and 2.57 (2m, 2H, C$_2$· C$\underline{H}_2$), 3.55 (m, 2H, C$_5$· C$\underline{H}_2$), 3.74 (s, 5H, C$\underline{H}_2$ and C$\underline{H}_3$O), 3.85 (t, 1H, C$_4$·$\underline{H}$), 4.38 (m, 1H, C$_3$·$\underline{H}$), 5.01 (t, 1H, C$_5$· O$\underline{H}$, exchangeable with D$_2$O), 5.30 (d, 1H, C$_3$· O$\underline{H}$, exchangeable with D$_2$O), 6.22 (t, 1H, J$_{1',2'}$=6.72 Hz, C$_1$·$\underline{H}$), 6.91–7.26 (m, 4H, C$_6$H$_4$), 8.25 (s, 1H, C$_8$$\underline{H}$), 11.92 and 11.96 (2s, 2H, 2×N$\underline{H}$CO, exchangeable with D$_2$O).

Analysis: Calcd for C$_{19}$H$_{21}$N$_5$O$_6$.1.5H$_2$O(442.40): C, 51.58; H, 5.47; N, 15.83. Found: C, 51.76; H, 4.94; N, 15.73.

EXAMPLE 22

Synthesis of 5'-O-(4,4'-dimethoxytrityl)-N$^2$-(substituted phenylacetyl)-2'-deoxyguanosine The N$^2$-(substituted phenylacetyl)-2'-deoxyguanosine (10 mmoles) prepared according to Example 21 was dried by co-evaporation with dry pyridine (2×30 ml) and dissolved in 80 ml of dry pyridine. To the resulting solution was added 4,4'-dimethoxytrityl chloride (15 mmoles) portionwise at room temperature and the reaction mixture was left stirring at room temperature for 20 hours. After removing pyridine under reduced pressure, the resulting residue was dissolved in 400 ml of methylene chloride and washed with 2×300 ml of 5% $NaHCO_3$. The organic layer was dried over anhydrous sodium sulfate and concentrated to near dryness. The product was purified on a silica gel column (5×40 cm) by gradient elution with 0–6% methylene chloride-methanol (700 ml). The desired fractions were collected, concentrated to ~30 ml and added dropwise to cooled hexane (0° C., 400 ml) to precipitate the product. The precipitated product was filtered, washed with hexane and air dried.

5'-0-(4,4'dimethoxytrityl)-$N^2$-(4-fluorophenylacetyl)-2'-deoxyguanosine (3d):

Yield: 83%; HPLC purity: 98.50% m.p. 150°–155° C. $R_f$=0.4 in methylene chloride- methanol (95:5,v/v) UV (EtOH): λ max 280 nm and 236 nm. IR (KBr): ν 1687 (vs, br, C=O of amides), 2900–3600 (NH, OH) $cm^{-1}$. $^1$H-NMR ($CDCl_3$): δ 2.34 and 2.50 (2m, 2H, $C_2$, $CH_2$), 3.26 (m, 2H, $C_5$, $CH_2$), 3.64 (s, 6H, 2×—$OCH_3$), 3.68 (s, 2 H,$CH_2$), 4.14 (m, 1H, $C_4$, $\underline{H}$), 4.57 (t, 1H, $C_3$, 6.08 (t, 1H, $C_1$, $\underline{H}$), 6.68–7.35 (m, 17H, of $C_6$ $\underline{H}_4$, and aromatic protons of DMTr), 7.85 (s, 1H, $C_8$ $\underline{H}$), 10.83 and 12.22 (2s, 2H, 2×CON$\underline{H}$—).

Analysis: Calcd for $C_{39}H_{36}N_5O_7F.0.5H_2O$(714.72): C, 65.53; H, 5.22; N, 9.80; F, 2.66 Found: C, 65.88; H, 5.62; N, 9.19; F, 2.60.

5'-O-(4,4'-dimethoxytrityl)-$N^2$-(4-bromophenylacetyl)-2'-deoxyguanosine (3e):

Yield: 78%; HPLC purity: 99.246% m.p. 150°–155° C. $R_f$=0.4 in methylene chloride- methanol (95:5,v/v) UV (EtOH): λ max 276 nm and 260 nm. IR (KBr): ν 1680 (vs, br, C=O of amides), 2900–3600 (NH, OH) $cm^{-1}$. $^1$H-NMR ($CDCl_3$): δ 2:30 and 2.55 (2m, 2H, $C_2$, $CH_2$), 3.26 (m, 2H, $C_5$, $CH_2$), 3.63 (s, 6H, 2×—$OCH_3$), 3.66 (s, 2H, $CH_2$), 4.13 (m, 1H, $C_4$, $\underline{H}$), 4.55 (m, 1H, $C_3$,$\underline{H}$), 6.06 (t, 1H, $C_1$, $\underline{H}$), 667–732 (m, 17H, of $C_6$ $\underline{H}_4$, and aromatic protons of DMTr), 7.85 (s, 1H, $C_8$ $\underline{H}$), 10.97 and 12.20 (2s, 2H, 2×CONH—).

Analysis: Calcd for $C_{39}H_{36}N_5O_7Br0.5H_2$ (775.64): C, 60.39; H, 4.81; N, 9.03; Br, 10.30 Found: C, 60.29; H, 5.12; N, 8.78; Br, 10.63.

5'-O-(4,4'-dimethoxytrityl)-$N^2$-(4-chlorophenylacetyl)-2'-deoxyguanosine (3f):

Yield: 55%. m.p. 150°–155° C. $R_f$=0.4 in methylene chloride- methanol (95:5,v/v) UV (EtOH): λ max 280 nm and 234 nm. IR (KBr): ν 1685 (vs, br, C=O of amides), 2900–3500 (NH, OH) $cm^{-1}$. $^1$H-NMR ($CDCl_3$): δ 2.36 and 2.54 (2m, 2H, $C_2$, $CH_2$), 3.28 (m, 2H, $C_5$, $CH_2$), 3.66 (s, 8H, 2×$OCH_3$, and $CH_2$), 4.15 (m, 1H, $C_4$, $\underline{H}$), 4.59 (m, 1H, $C_3$, $\underline{H}$), 6.09 (t, 1H, $J_{1',2}$=6.13 Hz, $C_1$, $\underline{H}$), 6.69–7.36 (m, 17H, of $C_6$ $\underline{H}_4$, and aromatic protons of DMTr), 7.84 (s, 1H, $C_8$ $\underline{H}$), 10.64 and 12.10 (2s, 2H, 2×CON$\underline{H}$—).

Analysis: Calcd for $C_{39}H_{36}N_5O_7Cl.0.5H_2O$ (731.18): C, 64.07; H, 5.48; N, 9.16; Cl, 4.58. Found: C, 64.06; H, 5.10; N, 9.59; Cl, 4.85

5'-O-(4,4'-dimethoxytrityl)-$N^2$-(3,4-dichlorophenylacetyl)-2'-deoxyguanosine (3g):

Yield: 65 %. m.p. 150°–155° C. $R_f$=0.4 in methylene chloride- methanol (95:5,v/v) UV (EtOH): λ max 282 nm and 234 nm. IR (KBr): ν 1687 (vs, br, C=O of amides), 2900–3500 (NH, OH) $cm^{-1}$. $^1$H-NMR ($CDCl_3$): δ 2.38 and 2.60 (2m, 2H, $C_2$, $CH_2$), 3.28 (m, 2H, $C_5$, $CH_2$), 3.71 (s, 8H, 2×—$OCH_3$ and $CH_2$), 4.14 (m, 1H, $C_4$, $\underline{H}$), 4.58 (m, 1H, $C_3$, $\underline{H}$), 6.23 (t, 1H, $J_{1',2}$=6.22 Hz, $C_1$, $\underline{H}$), 6.72–7.42 (m, 16H, of $C_6$ $\underline{H}_3$, and aromatic protons of DMT), 7.82 (s, 1H, $C_8$ $\underline{H}$), 11.33 and 12.07 (2s, 2H, 2×CON$\underline{H}$—).

Analysis: Calcd for $C_{39}H_{35}N_5O_7Cl_2$ (756.62): C, 61.91; H, 4.66; N, 9.26; Cl, 9.37. Found: C, 61.58; H, 5.26; N, 8.70; Cl, 9.12

5'-O-(4,4'-dimethoxytrityl)-$N^2$-(4-methoxyphenylacetyl)-2'-deoxyguanosine (3c):

Yield: 71%. m.p. 148°–156° C. $R_f$=0.5 in methylene chloride- methanol (95:5,v/v) UV (EtOH): λ max 281 nm and 236 nm. IR (KBr): ν 1687 (vs, br, C=O of amides), 2900–3600 (NH, OH) $cm^{-1}$. $^1$H-NMR ($CDCl_3$): δ 2.42 and 2.63 (2m, 2H, $C_2$, $CH_2$), 3.28 (m, 2H, $C_5$, $CH_2$), 3.65 (s, 8H, 2×—$OCH_3$ and $CH_2$), 3.72 (s, 3H, $OCH_3$), 4.15 (m, 1H, $C_4$, $\underline{H}$), 4.61 (m, 1H, $C_3$, $\underline{H}$), 6.13 (t, 1H, $J_{1',2}$=6.55 Hz, $C_1$, $\underline{H}$), 6.69–7.36 (m, 17H, of $C_6$ $\underline{H}_4$, and aromatic protons of DMTr), 7.80 (s, 1H, $C_8$ $\underline{H}$).

Analysis: Calcd for $C_{39}H_{37}N_5O_7.0.5H_2O$ (696.73): C, 67.23; H, 5.50; N, 10.05. Found: C, 67.49; H, 5.84; N, 9.48.

EXAMPLE 23

Synthesis of $N^2$-(substituted phenylacetyl)-5'-0-(4,4'-dimethoxytrityl)-2'-deoxyguanosine-3'-0-(N,N-diisopropyl)-β-cyanoethylphosphoramidite The nucleosides of Example 22 (2 mmoles) were dried under high vacuum for 5 hours and dissolved in dry methylene chloride (10 ml) under argon. 2-cyanoethyl-N,N,N',N'-tetraisopropylphosphorodiamidite (1.5 ml, 4.36 mmoles) and 5-methylthiotetrazole (0.25 g, 2.27 mmoles) were added and stirred at room temperature overnight. The reaction mixture was diluted with $CH_2Cl_2$ (50 ml), washed with sodium bicarbonate solution 7% (3×50 ml), dried over anhydrous sodium sulfate and evaporated to dryness. The residue was further dried for 5 hours in high vacuum, dissolved in ethyl acetate (10 ml) and transferred to a silica gel column (70–230 mesh, preheated at 100°–120° C. overnight, packed with ethyl acetate). After elution with more ethyl acetate the desired fractions were collected, evaporated to dryness and further dried in high vacuum for 5 hours to yield the phosphoramidite.

$N^2$-(4 fluorophenylacetyl)-5'-0-(4,4'-dimethoxytrityl)-2'-deoxyguanosine-3'-0-(N,N-diisopropyl)-β-cyanoethyl-phosphoramidite (4d):

Yield: 78% m.p. 90°–100° C. (dec.) $R_f$=0.5 in $CH_2Cl_2$/MeOH (95:5, v/v) UV (EtOH): λ max 276 nm and 235 nm IR (KBr): ν 1694 (vs, br, C=0 of amides), 2256 (—C≡N group), 2945 and 3184 (vs. NH) $cm^{-1}$. $^1$H-NMR ($CDCl_3$): 5 δ 1.11 and 1.31 (m, 12H, 2CH—C≡N $(CH_3)_2$), 2.44 and 2.72 (2m, 4H, $C_2$, $CH_2$, —$CH_2$ $CH_2$ CN), 3.28 and 3.75 (m, 6H, $C_5$, $CH_2$, 233 $CH(CH_3)_2$, p- O—$CH_2$ $CH_2$), 3.74 (s, 6 H, 2×—$OCH_3$), 3.75 (s, 2H, $COCH_2$), 4.15 (m, 1H, $C_4$, $\underline{H}_2$), 4.82 (m, 1H, $C_3$, $\underline{H}$), 6.19 (t, 1H, J=3.6 Hz, $C_1$, $\underline{H}$), 6.73–7.44 (m, 17H, $C_6$ $\underline{H}_4$, and aromatic protons of DMT), and 7.78 (d, 1H, C$_8$ H) $^{31}$P-NMR (CDCl$_3$): δ 146.38 ppm and 147.19 ppm.

Analysis: Calcd for C$_{48}$H$_{53}$N$_7$O$_8$PF (905.92): C, 63.63; H, 5.90; N, 10.82; P, 3.42; F, 2.10. Found: C, 63.20; H, 6.11; N, 10.49; P, 3.23; F, 1.91. HPLC: Retention times of 8.96 min and 10.20 min corresponding to two diastereoisomers (99.26% purity). Conditions: C$_{18}$ Ultrasphere column (Rainin), 5μ particles, 4.6 mm×25 cm.

Bottle A: 0.1M Ammonium Acetate pH 6.9
Bottle B: Acetonitrile
Program: Flow rate 1 ml/min 0–20 min at 80% B

N$^2$(4-bromophenylacetyl)-5'-O-(4,4'-dimethoxytrityl)-2'-deoxyguanosine-3'-O-(N,N-diisopropyl)-β-cyanoethyl-phosphoramidite (4e):

Yield: 83% m.p. 80°–90° C. (dec.) R$_f$=0.6 in CH$_2$Cl$_2$/MeOH (95:5, v/v) UV (EtOH): λ max 282 nm and 236 nm IR (KBr): ν 1694 (vs, br, C=O of amides), 2256 (—C≡N group), 2980 and 3200 (vs. NH) cm$^{-1}$. $^1$H-NMR(CDCl$_3$): δ 1.11 and 1.28 (m, 12H, 2CH (CH$_3$)$_2$), 2.40 and 2.70 (2m, 4H, C$_2$, CH$_2$, —CH$_2$ CH$_2$ CN), 3.28 and 3.75 (m, 14H, C$_5$, CH$_2$, 2×CH (CH$_3$)$_2$, 2×—OCH$_3$, CH$_2$ C$_6$H$_5$, - p O CH$_2$ CH$_2$), 4.25 (m, 1H, C$_4$, H), 4.70 (m, 1H, C$_3$, H), 6.18 (t, 1H, C$_1$, H), 6.73–7.45 (m, 17H, C$_6$ H$_4$, and aromatic protons of DMT), and 7.80 (d, 1H, C$_8$ H) $^{31}$P-NMR (CDCl$_3$): δ 146.35 ppm and 147.20 ppm.

Analysis: Calcd for C$_{48}$H$_{53}$N$_7$O$_8$PBr (966.83): C, 59.63; H, 5.53; N, 10.14; P, 3.20; Br, 8.27. Found: C, 59.28; H, 5.89; N, 9.75; P, 3.08; Br, 8.53. HPLC: Retention times of 11.40 min and 12.78 min corresponding to two diastereoisomers (99.12% purity). Conditions: C$_{18}$ Ultrasphere column (Rainin), 5μ particles, 4.6 mm×25 cm.

Bottle A: 0.1M Ammonium Acetate pH 6.9
Bottle B: Acetonitrile
Program: Flow rate 1 ml/min

N$^2$-(4-chlorophenylacetyl)-5'-O-(4,4'-dimethoxytrityl)-2'-deoxyguanosine-3'-O-(N,N-diisopropyl)-β-cyanoethyl-phosphoramidite (4f):

Yield: 70% m.p. 75°–85° C. (dec.) R$_f$=0.5 in CH$_2$Cl$_2$/MeOH (95:5, v/v) UV (EtOH): λ max 280 nm and 236 nm IR (KBr): ν 1694 (vs, br, C=O of amides), 2250 (—C≡N group), 2966 and 3191 (vs. NH) cm$^{-1}$. $^1$H-NMR(CDCl$_3$): δ 1.11 and 1.31 (m, 12H, 2CH(CH$_3$)$_2$), 2.44–271 (2m, 4H, C$_2$, CH$_2$, and —CH$_2$CH$_2$CN), 3.27 and 3.65 (m, 6H, C$_5$, C H$_2$, 2×CH (CH$_3$)$_2$ and p—O—CH$_2$CH$_2$), 3.71 (s, 6H, 2×—OCH$_3$), 3.78 (s, 2H, CH$_2$), 4.31 (m, 1H, C$_4$, H), 4.82 (m, 1H, C$_3$, H), 6.18 (t, 1H, C$_1$, H), 6.73–7.44 (m, 17H, C$_6$ H$_4$, and aromatic protons of DMT), and 7.77 (d, 1H, C$_8$ H) $^{31}$P-NMR (CDCl$_3$): δ 146.37 ppm and 147.20 ppm. HPLC: Retention times of 10.58 min and 11.85 min corresponding to two diastereoisomers (99.73% purity). Conditions: C$_{18}$ Ultrasphere column (Rainin), 5μ particles, 4.6 mm×25 cm.

Bottle A: 0.1M Ammonium Acetate pH 6.9
Bottle B: Acetonitrile
Program: Flow rate 1 ml/min 0–20 min at 80% B Analysis: Calcd for C$_{48}$H$_{53}$N$_7$O$_8$PCl(922.37): C, 62.49; H, 5.79; N, 10.63; P, 3.36; Cl 3.84. Found: C, 61.96; H, 6.21; N, 10.38; P, 3.25; Cl, 3.45

N$^2$-(3,4-dichlorophenylacetyl)-5-O-(4,4'-dimethoxytrityl)-2'-deoxyguanosine-3'-O-(N,N-diisopropyl)-β-cyanoethyl-phosphoramidite (4g):

Yield: 75% m.p. 90°–100° C. (dec.) R$_f$=0.5 in CH$_2$Cl$_2$/MeOH (95:5, v/v) UV (EtOH): λ max 280 nm and 236 nm IR (KBr): ν 1694 (vs, br, C=O of amides), 2250 (—C≡N group), 2966 and 3185 (vs. NH) cm$^{-1}$. $^1$H-NMR(CDCl$_3$): δ 1.11–1.29 (m, 12H, 2×CH (CH$_3$)$_2$), 2.45–2.72 (2m, 4H, C$_2$, CH$_2$, and —CH$_2$CH$_2$CN), 3.28 and 3.62 (m, 6H, C$_5$, C H$_2$, 2×CH (CH$_3$)$_2$, and p—O—CH$_2$CH$_2$), 3.74 (s, 6H, 2×—OCH$_3$), 3.79 (s, 2H, CH$_2$), 4.15 (m, 1H, C$_4$, H), 4.78 (m, 1H, C$_3$, H), 6.19 (t, 1H, J$_{1',2}$=6.12, C$_1$, H), 6.73–7.76 (m, 16H, C$_6$H$_3$, and aromatic protons of DMT) and 7.80 (d, 1H, C$_8$H) $^{31}$P-NMR (CDCl$_3$): δ 146.27 ppm and 147.21 ppm.

Analysis: Calcd for C$_{48}$H$_{52}$N$_7$O$_8$PCl$_2$(956.83): C, 60.25; H, 5.48; N, 10.25; P, 3.24; Cl, 7.41. Found: C, 60.23; H, 5.88; N, 9.90; P, 3.40; Cl, 7.17. HPLC: Retention times of 12.98 min and 14.52 min corresponding to two diastereoisomers (99.67% purity). Conditions: C$_{18}$ Ultrasphere column (Rainin), 5μ particles, 4.6 mm×25 cm.

Bottle A: 0.1M Ammonium Acetate pH 6.9
Bottle B: Acetonitrile
Program: Flow rate 1 ml/min 0–20 min at 80% B

N$^2$-(4-methoxyphenylacetyl)-5-O-(4,4'-dimethoxytrityl)-2'-deoxyguanosine-3'-O-(N,N-diisopropyl)-β-cyanoethyl-phosphoramidite (4c):

Yield: 80% m.p. 80°–90° C. (dec.) R$_f$=0.6 in CH$_2$Cl$_2$/MeOH (95:5, v/v) UV (EtOH): λ max 276 nm and 236 nm IR (KBr): ν 1687 (vs, br, C=O of amide), 1730 (s, C=O of ring amide), 2256 (—C≡N group), 2952 (vs. NH) cm$^{-1}$. $^1$H-NMR(CDCl$_3$): δ 1.17(m, 12H, 2×CH (CH$_3$)$_2$), 2.40 and 2.75 (2m, 2H, C$_2$, CH$_2$), 2.68 (2t, 2H, —CH$_2$CH$_2$CN), 3.30 and 3.78 (m, 17H, C$_5$, CH$_2$, 2×CH (CH$_3$)$_2$, 2×—OCH$_3$, C H$_2$C$_6$H$_4$—OCH$_3$, p—O—CH$_2$CH$_2$), 4.38 (m, 1H, C$_4$, H), 4.75 (m, 1H, C$_3$, H), 6.20 (dt, 1H, J$_{1',2}$=4.74, C$_1$, H), 6.74–7.40 (m, 17H, C$_6$H$_4$, and aromatic protons of DMT), and 7.78 (d, 1H, C$_8$H) $^{31}$P-NMR (CDCl$_3$): δ 147.43 ppm and 148.00 ppm.

Analysis: Calcd for C$_{49}$H$_{56}$N$_7$O$_9$P (918): C, 64.11; H, 6.15; N, 10.68; P, 3.38. Found: C, 64.39; H, 6.44; N, 10.97; P, 3.28. HPLC: Retention times of 8.90 min and 10.01 min corresponding to two diastereoisomers (99.53% purity). Conditions: C$_{18}$ Ultrasphere column (Rainin), 5μ particles, 4.6 mm×25 cm.

Bottle A: 0.1M Ammonium Acetate pH 6.9
Bottle B: Acetonitrile
Program: Flow rate 1 ml/min 0–20 min at 80% B

EXAMPLE 24

Synthesis of $N^2$-(4-bromo and 4-fluorophenylacetyl)-5'-O-(4,4'-dimethoxytrityl)-2'-deoxyguanosine-3'-(N,N-diisopropyl)-methyl phosphonamidite

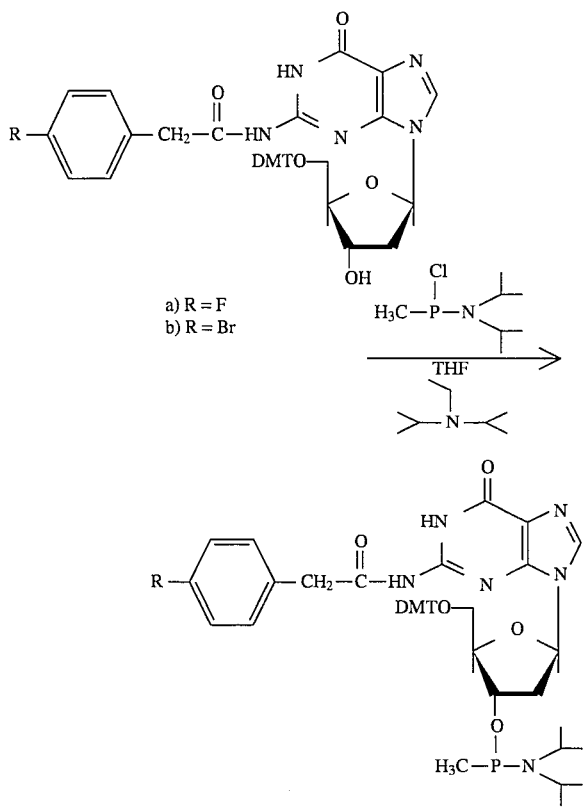

a) R = F
b) R = Br

The nucleosides of Example 22 (2 mmoles) were dried by successive coevaporations with pyridine, toluene and THF. The dried residue was dissolved in dry THF (10 ml). Redistilled N,N,N-diisopropylethylamine (1.8 ml) was added, followed by the addition of methylmonochloro-N,N-diisopropylphosphonamidite (1.2 ml) dropwise using a syringe with a constant stirring under argon at room temperature over 5 minutes. After 3 hours of stirring, the reaction mixture was diluted with ethyl acetate (50 ml), washed with 5% $NaHCO_3$ solution (2×50 ml) and dried over $Na_2SO_4$. The crude material was dissolved in ethyl acetate and transferred to a silica gel column (2×30 cm, 70–230 mesh, 60Å, preheated at 100°–120° C. overnight) in ethyl acetate. Elution with ethyl acetate gave the desired material. The material was collected and evaporated to dryness and was put on high vacuum for 5 hours to yield the phosphonamidite.

$N^2$-(4-Fluorophenylacetyl)-5'-O-(4,4'-dimethoxytrityl)-2'-deoxyguanosine-3'-(N,N-diisopropyl)-methyl phosphonamidite Yield: 68% m.p. 100°–110° C. $R_f$=0.6 in $CH_2Cl_2$:MeOH (95:5, v/v) UV (EtOH): λ max 276 m and 236 nm IR (KBr): ν 1694 (vs, br, CO of amides), 3000–3170 (vs, br, NH) $cm^{-1}$. $^1$H-NMR ($CDCl_3$): δ 0.93–1.20 (m, 15 H, P—$CH_3$ and C$H_3$ iPr), 2.42 and 2.57 (2m, 2H, $C_{2'}$ $H_2$), 3.16 and 3.36 (m, 4H, $C_5$, $CH_2$, 2×CH iPr), 3.75 (s, 8H, $CH_2$ $C_6H_4$ and 2×$OCH_3$ DMTr), 4.15 (m, 1H, $C_{4'}$ H), 4.72 (m, 1H, $C_{3'}$ H), 6.19 (m, 1H, $C_{1'}$ H), 6.75–7.46 (m, 17 H, $C_6H_4$ and aromatic protons of DMTr), and 7.78 (s 1H, $C_8H$). $^{31}$P-NMR ($CDCl_3$): δ 118.90 ppm and 117.35 ppm. Calcd. for $C_{46}H_{52}N_6O_7PF$ (850.9): C, 64.93; H, 6.16; N, 9.88; P, 3.64; F, 2.23 Found: C, 64.73; H, 6.48; N, 9.58; P, 3.51; F, 2.03 HPLC retention times of 12.61 min and 13.01 minutes, corresponding to two diastereoisomers (99.10% purity). Conditions: C18 Ultrasphere column (Beckman Instruments) 5μ particles, 4.6 mm×25 cm. Bottle A: 0.1M Ammonium acetate (pH 6.9); Bottle B: Acetonitrile. Program: Flow rate 1 ml/min. 0–20 min at 80% B.

$N^2$-(4-Bromophenylacetyl)-5'-O-(4, 4'-dimethoxytrityl)-2'-deoxyguanosine-3'-(N,N-diisopropyl)-methyl phosphonamidite Yield: 60% m.p. 110°–120° C. $R_f$=0.6 in $CH_2Cl_2$:MeOH (95:5, v/v) UV (EtOH): λ max 281, 276 m and 235 nm IR (KBr): ν 1690 (vs, br, CO of amides), 3000–3100 (vs, br, NH) $cm^{-1}$. $^1$H-NMR ($CDCl_3$): δ 0.94–1.29 (m, 15H, P—C$H_3$ and $CH_3$ iPr), 2.44 and 2.62 (2m, 2H, $C_{2'}$ $CH_2$), 3.20 and 3.40 (m, 4H, $C_5$, $CH_2$, 2×CH iPr), 3.74 (s, 8H, $CH_2$ $C_6H_4$ and 2×$OCH_3$ DMTr), 4.11 (m, 1H, $C_4$H), 4.58 (m, 1H, $C_{3'}$ H), 6.12 (m, 1H, $C_{1'}$ H), 6.75–745 (m, 17H, $C_6H_4$ and aromatic protons of DMTr), and 7.78 (s 1H, $C_8H$). $^{31}$P-NMR ($CDCl_3$): δ 119.26 ppm and 117.56 ppm. HPLC retention times of 17.20 min and 18.18 minutes, corresponding to two diastereisomers (99.10% purity). Conditions: C18 Ultrasphere column (Beckman Instruments) 5μ particles, 4.6 mm×25 cm. Bottle A: 0.1M Ammonium acetate (pH 6.9); Bottle B: Acetonitrile. Program: Flow rate 1 ml/min. 0–20 min at 80% B.

EXAMPLE 25

Synthesis of 5'-O-(dimethoxytrityl)-N²-(4-fluoro or 4-bromophenylacetyl)-2'-deoxyguanosine-3'-hydrogen phosphonate triethylammonium salt

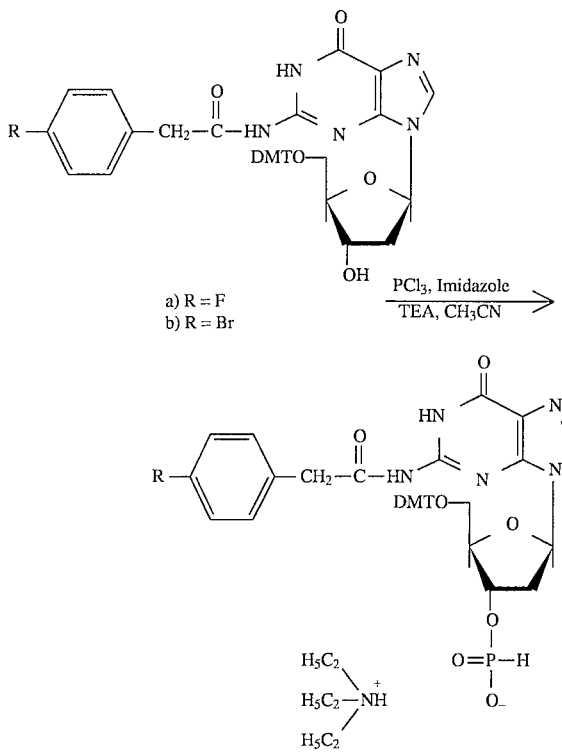

a) R = F
b) R = Br

Imidazole (3.6 gm, 53 mmoles) was dissolved in acetonitrile (100 ml) and at 0° C., $PCl_3$ (1.4 ml, 16 mmoles) and TEA (7.8 ml) were added. The reaction mixture was stirred for 30 minutes; then DMT $dG^{FPA}$ (3d) or DMT $dG^{BPA}$ (3e) prepared as in Example 22 (3.7 mmoles) in acetonitrile (100 ml) was added dropwise over a 30 minute period. The reaction mixture was stirred at room temperature for 4 hours. Water (25 ml) was added and stirring continued for another 30 minutes. The solution was evaporated, then coevaporated twice with 50 ml pyridine/TEA (4:1, v/v). The residue was dissolved in $CHCl_3$ (200 ml), washed with water (100 ml), dried over $Na_2SO_4$, filtered and evaporated. The residue after evaporation was dissolved in $CHCl_3$ (10 ml) and precipitated with ether (500 ml). The filtered product was washed with ether and dried to give the desired product.

5'-O-(Dimethoxytrityl)-N²-(4-fluorophenylacetyl)-2'-deoxyguanosine-3'-hydrogen phosphonate triethylammonium salt Yield: 78% m.p. 120°–135° C. UV (EtOH): λ max 275 nm and 234 nm. ¹H-NMR ($CDCl_3$): δ 1.23 (t, 3H, $NCH_2CH_3$), 2.65 and 2.82 (2m, 2H, $C_{2'}$ $CH_2$), 3.02 (q, 2H, $NCH_2CH_3$), 3.46 (m, 2H, $C_5,CH_2$), 3.70 (s, 6H, 2×$OCH_3$), 3.80 (s, 2H, $CH_2C_6H_4$), 4.31 (m, 1H, $C_{4'}$ H), 5.26 (m, 1H, $C_{3'}$ H), 6.18 (t, 1H, $C_1H$), 6.86 (d, 1H, $J_{P-H}$=555 Hz, H-P), 6.67–7.34 (m, 17H, DMT aromatic protons and $C_6H_4CH_2$), 7.99 (s, 1H, $C_8H$), and 12.20 (br, s, 2H, 2×N HCO). ³¹P-NMR ($CDCl_3$): δ 3.99 ppm and –1.16 ppm $J_{H-P}$=624.9 Hz.

5'-(Dimethoxytrityl)-N²-(4-bromophenylacetyl)-2'-deoxyguanosine-3'-hydrogen phosphonate triethylammonium salt Yield: 70% m.p. 120°–135° C. UV (EtOH): λ max 275 nm and 234 nm. ¹H-NMR ($CDCl_3$): δ 1.24 (t, 3H, $NCH_2CH_3$), 2.67 and 2.96 (2m, 2H, $C_{2'}$ $CH_2$), 3.05 (q, 2H, $NCH_2CH_3$), 3.31 (m, 2H, $C_5,CH_2$), 3.78 (s, 6H, 2×$OCH_3$) 3.81 (s, 2H, $CH_2C_6H_4$), 4.26 (m, 1H, $C_{4'}$ H), 5.27 (m, 1H, $C_{3'}$ H), 6.25 (t, 1 H, $C_1H$), 6.86 (d, 1H, $J_{P-H}$=555 Hz, H-P), 6.70–7.45 (m, 17H, DMT aromatic protons and $C_6H_4CH_2$) and 7.93 (s, 1H, $C_8H$). ³¹P-NMR ($CDCl_3$): δ 3.84 ppm and –1.31 ppm $J_{H-P}$=624.9 Hz.

EXAMPLE 26

Synthesis of 5'-O-(dimethoxytrityl)-N²-(4-fluorophenylacetyl)-2'-deoxyguanosine-3'-succinate (DMT-$dG^{FPA}$-3'-Succinate)

DMT-$dG^{FPA}$ (3d) prepared as in Example 22 (1.65 g, 2.38 mmoles), succinic anhydride (0.714 g, 14 mmoles), and DMAP (0.145 g, 1.19 mmoles) were dissolved in dry pyridine (25 ml) and stirred at room temperature for 24 hours. The pyridine was evaporated off and the residue was coevaporated with dry toluene (3×25 ml). The gummy residue was dissolved in $CH_2Cl_2$ (100 ml) and washed successively with saturated NaCl solution (3×25 ml) and water (1×70 ml). The $CH_2Cl_2$ solution was dried over anhydrous $Na_2SO_4$ and was evaporated. The residue was dissolved in $CH_2Cl_2$ (20 ml) and was precipitated at room temperature into rapidly stirred hexane (300 ml). The product was filtered and dried under vacuum to yield 1.15 g (60%) of DMT-$dG^{FPA}$-3'-Succinate.

The product was characterized as follows: m.p. 130°–140° C. (dec.); UV (EtOH): λ max 280 nm and 236 nm; IR (KBr): ν 1714 (vs, br, C=O of amide and acid), 2800–3600 (NH, OH) cm⁻¹. ¹H-NMR ($CDCl_3$): δ 2.62 (m, 6H, $C_2$, $CH_2$, $CH_2CH_2$), 3.30 (m, 2H, $C_5$, $CH_2$), 3.53 (s, 2H, $CH_2C_6H_4$), 3.78 (s, 6H, 2×$OCH_3$), 4.19(m, 1H, $C_4$, H), 5.36 (m, 1H, $C_3'$, H), 5.99 (m, 1H, $C_{1'}$ H), 6.72–7.34(m, 17H, DMT group and $C_6H_4$)and 7.80 (s, 1H, $C_8H$).

EXAMPLE 27

Synthesis of N²-(4-bromophenylacetyl)-5'-O-(dimethoxytrityl)-2'-deoxyguanosine-3'-succinate (DMT-$dG^{BPA}$-3'-Succinate)

DMT-$dG^{BPA}$ (3e) prepared as in Example 22 (2 g, 2.61 mmoles), succinic anhydride (0.783 g, 7.83 mmoles), and DMAP (0.160 g, 1.31 mmoles) were dissolved in dry pyridine (20 ml) and stirred at room temperature for 24 hours. The pyridine was evaporated off and the residue was coevaporated with dry toluene (3×25 ml). The gummy residue was dissolved in $CH_2Cl_2$ (100 ml) and washed successively with saturated NaCl solution (3×100 ml) and water (1×100 ml). The $CH_2Cl_2$ solution was dried over anhydrous $Na_2SO_4$ and was evaporated. The residue was dissolved in $CH_2Cl_2$ (20 ml) and was precipitated at room temperature into rapidly stirred hexane (300 ml). The product was filtered and dried under vacuum to yield 1.80 g (80%) of DMT-$dG^{BPA}$-3'-Succinate.

The product was characterized as follows: m.p. 140°× 150° C. (dec.); UV (EtOH): λ max 280 nm and 236 nm; IR (KBr): ν 1700 (vs, br, C=O of amide and acid), 2800–3600 (NH, OH) cm⁻¹. ¹H-NMR ($CDCl_3$): δ 2.64 (m, 6H, $C_2$, $CH_2$, $CH_2CH_2$), 3.30 (m, 2H, $C_5$, $CH_2$), 3.54(s, 2H, C $\underline{H}_2C_6H_4$), 3.78 (s, 6H, 2×OC$\underline{H}_3$), 4.22 (m, 1H, C$_4$, $\underline{H}$), 5.37 (m, 1H, C$_3$, $\underline{H}$), 5.91 (m, 1H, C$_1$, $\underline{H}$), 6.75–7.41 (m, 17H, DMT group and C$_6\underline{H}_4$) and 7.79 (s, 1H, C$_8\underline{H}$).

EXAMPLE 28

Stability of Deoxyguanosine derivatives during DNA synthesis

A 35-mer was synthesized on a Pharmacia Gene Assembler at 0, 1 and 2 weeks and the coupling efficiencies were determined by released trityl colors, as well as by the analysis of the synthesized oligonucleotides by capillary electrophoresis. There was no discernible difference among the three deoxyguanosine derivatives employed, as shown in Table 1.

TABLE 1

| dG derivative | Duration of reagent on the DNA Synthesizer | DMT Coupling Efficiencie s |
|---|---|---|
| dG$^{Phenylacetyl}$ | 0 week | 98.8% |
| dG$^{Methoxyphenlacetyl}$ | " | 98.9% |
| dG$^{isobutyl}$ | " | 99.1% |
| dG$^{PA}$ | 1 week | 98.9% |
| dG$^{MPA}$ | " | 98.6% |
| dG$^{ibu}$ | " | 99.0% |
| dG$^{PA}$ | 2 weeks | 99.0% |
| dG$^{MPA}$ | " | 99.0% |
| dG$^{ibu}$ | " | 98.9% |

Similar results were obtained in the synthesis of a 35-mer on the Oligo 1000 DNA synthesizer, with no significant difference being observed among the three protecting groups. The oligonucleotides synthesized using dG$^{PA}$ phosphoramidite were quantitatively phosphorylated by the 5'-terminal transferase and were quantitatively extended at the 3'-end by the 3'-terminal transferase.

In addition, 35-mers were synthesized using the 4-bromophenylacetyl- and the 4-fluorophenylacetyl-derivatives on an Oligo-1000 at 0, 1 and 2 weeks and the coupling efficiencies were determined by the released trityl colors as well as by the analysis of the synthesized oligonucleotides by capillary electrophoresis. There was no discernible difference between the performance of the new derivatives and the conventional G$^{ibu}$ derivative.

The integrity of the oligonucleotides was established by digesting a 35-mer to the individual nucleosides and analyzing them by reverse phase HPLC. There was acceptable correlation between the observed nucleoside composition and the theoretically expected values, as shown in Table 2.

TABLE 2

|  | C | G | T | A |
|---|---|---|---|---|
| Expected | 11 | 8 | 9 | 7 |
| dG$^{PA}$, dC$^{AC}$ | 10.35 | 8.23 | 10.01 | 6.50 |
| dG$^{MPA}$, dC$^{AC}$ | 10.28 | 8.21 | 9.65 | 6.84 |
| dG$^{ibu}$, dC$^{bz}$ | 10.24 | 8.25 | 9.51 | 6.65 |

The integrity of oligonucleotides prepared using the 4-bromophenylacetyl- and and 4-fluorophenylacetyl-derivatives was established by digesting a 35-mer to the individual nucleosides and analyzing them by reverse phase HPLC. There was acceptable correlation between the observed nucleoside composition and the theoretically expected values (as shown in Table 3). In addition, the oligonucleotides performed well in applications, such as PCR and DNA sequencing.

TABLE 3

|  | Observed Value | | |
|---|---|---|---|
| Theoretical Value | dG$^{ibu}$ containing oligonucleotide | dG$^{FPA}$ containing oligonucleotide | dG$^{BPA}$ containing oligonucleotide |
| C  11 | 10.23 | 10.37 | 10.19 |
| G  8 | 8.12 | 8.10 | 8.29 |
| T  9 | 9.20 | 9.43 | 9.44 |
| A  7 | 6.69 | 6.76 | 6.69 |

EXAMPLE 29

Synthesis of RNA

An RNA 10mer was synthesized using the rG$^{PA}$ phosphoramidite of Example 10 on a Pharmacia Gene Assembler following the procedure described in Scaringe, S. A. et al., *Nucleic Acid Research* 18:5433–5441 (1990). The coupling time was 12 minutes. Cleavage and deprotection was performed using NH$_4$OH/EtOH (3:1) for 2 hours at 55° C. The 2'-protecting group was removed using 1.0M tetrabutyl ammonium fluoride in THF for 5 hours at room temperature. The resultant product (after HPLC purification of the product with the DMT group still in place) was chemically and physically indistinguishable from a 10 mer synthesized using commercially-available ribonucleotides.

HPLC: Retention time 20.85 minutes. Conditions: C$_{18}$ Ultrasphere column (Beckman Instruments), 5μ particles, 4.6 mm×25 cm. Bottle A: 0.1M Ammonium Acetate (pH 6.9); Bottle B: Acetonitrile. Program: Flow rate 1 ml/min; 0–25 min gradient to 50% B, 25–27 min at 50% B, 27–30 min gradient to 0% B, 30–32 min at 0% B.

EXAMPLE 30

Synthesis of Methylphosphonate Oligonucleotide

A 2 mer methylphosphonate was synthesized on a Pharmacia Gene Assembler using G$^{PA}$ methyl phosphonamidite prepared according to the procedure of Example 19, using a procedure as described in Agarwal, S. & Goodchild, J., *Tetrahedron Letters* 28:3539 (1987). The G$^{PA}$ was dissolved in dry THF, instead of dry acetonitrile. The procedure for synthesis was the same as for regular DNA, except that the coupling time was 5 minutes (instead of 2 minutes). After synthesis, the oligonucleotide was cleaved and deprotected with 1 ml EDA/EtOH (1:1) for one hour at room temperature. HPLC analysis of the product with the DMT protecting group in place confirmed a 58.08% percent yield of the desired product. The HPLC retention time was 24.35 minutes; the protocol was the same as in Example 29.

EXAMPLE 31

Synthesis of Oligonucleotide Using H-Phosphonate

A 21-mer was synthesized using conventional hydrogen phosphonate chemistry and the hydrogen phosphonate product prepared according to the procedure of Example 20. After synthesis, the oligonucleotide was cleaved and deprotected with MeNH$_2$/NH$_4$OH for ten minutes at room temperature. The resultant product was chemically and physically indistinguishable from a 21-mer synthesized using commercially-available H-phosphonates. The HPLC retention time (with the DMT protecting group in place) was 16.19 minutes; the protocol was the same as in Example 29.

EXAMPLE 32

Determination of Deprotection Kinetics

To determine the time required for complete deprotection, an oligonucleotide containing 50% dG was used. As the results in Table 4 show, by using the derivatives of the present invention with methylamine or MeNH$_2$/NH$_4$OH the deprotection time is reduced. This definitely speeds up the production of a large number of oligonucleotides used in various applicaions. Such as Human Genome Sequencing, PCR amplification of DNA, antisense nucleic acids based therapeuic agents, etc.

TABLE 4

| Protected G derivative | Time Required For Deprotection at 25° C. | | |
|---|---|---|---|
| | Methylamine/ Ammonia | Methylamine | NH$_4$OH |
| G$^{ibu}$ (Conventional Chemistry) | 75 min | 60 min | 72 h |
| G$^{Phenylacetyl}$ | 25 min | 15 min | 20 h |
| G$^{4\text{-Methoxyphenylacetyl}}$ | 25 min | 15 min | 20 h |
| G$^{3\text{-Methoxyphenylacetyl}}$ | 25 min | 15 min | 20 h |
| G$^{4\text{-Bromophenylacetyl}}$ | 15 min | 7 min | 8 h |
| G$^{4\text{-Fluorophenylacetyl}}$ | 15 min | 7 min | 8 h |
| G$^{4\text{-Chlorophenylacetyl}}$ | 15 min | 7 min | 8 h |
| G$^{3,4\text{-Dichlorophenylacetyl}}$ | 15 min | 7 min | 8 h |

The remarkable advantage in the use of the compositions and methods of the invention is demonstrated by a comparison with the heretofore-known compositions and methods as shown in Table 5.

TABLE 5

CLEAVAGE AND DEPROTECTION OF SUPPORT BOUND OLIGONUCLEOTIDES

| Protecting Groups (R$_1$, R$_2$, R$_3$) | Cleavage and Deprotection Reagent | Time Required for Cleavage | Time Required for Deprotection |
|---|---|---|---|
| A$^{bz}$, C$^{bz}$, G$^{ibu}$ | Ammonia | 1 h at 25° C. | 6 h at 55° C. |
| A$^{dmf}$, C$^{ibu}$, G$^{dmf}$ | Ammonia | 1 h at 25° C. | 1 h at 55° C. or 8 h at 25° C. |
| A$^{pac}$, C$^{ibu}$, G$^{pac}$ | Ammonia | 1 h at 25° C. | 1 h at 70° C. or overnight at 25° C. |
| A$^{tBPAC}$, C$^{tBPAC}$, G$^{tBPAC}$ | Ammonia | 1 h at 25° C. | 15 min at 55° C. |
| A$^{bz}$, C$^{Ac}$, G$^{ibu}$ | Methylamine or Methylamine/ Ammonia | 5 min at 25° C. | 5 min at 65° C. |
| A$^{bz}$, C$^{Ac}$, G$^{Phenylacetyl}$ or G$^{substituted}$ Phenylacetyl | Methylamine or Methylamine/ Ammonia | 5 min at 25° C. | <30 sec at 65° C. or 7 min–25 min at 25° C. |

EXAMPLE 33

Loading Amino-CPG Support with DMT-dG$^{PA}$-3'-succinate or DMT dG-$^{MPA}$-3'-succinate The succinylated deoxyribonucleotide of Example 5 (0.157 g, 0.2 mmole) was dissolved in dry dioxane (1 ml) containing (50 µl) pyridine and p-nitrophenol (28 mg, 0.2 mmole). DCC (103 mg, 0.5 mmole) was added and stirred overnight. The supernatant was added to LCAA-CPG solid support (1 g) suspended in DMF (4 ml), TEA (0.2 ml) was added and the mixture stirred overnight. The support was filtered and washed with DMF (3×7 ml), methanol (3×7 ml) and ether (3×7 ml) and dried using an oil pump. A DMT assay showed a nucleoside loading of 36.33 µmoles/g. The solid support (0.4 g) prepared as indicated was mixed with pyridine (4 ml), acetic anhydride (0.2 ml) and DMAP (20 mg) and stirred overnight at room temperature. The solid support was filtered, washed with methanol (3×7 ml) and ether (3×7 ml) and dried. A ninhydrin test to detect free amino groups was negative, indicating the successful capping of the amino groups. A further DMT assay showed a nucleoside loading of 38.93 µmole/g. DMT dG$^{MPA}$ succinate of Example 6 was loaded on CPG by following the same procedure.

EXAMPLE 34

Loading Amino-CPG support with DMT-dG$^{BPA}$ or DMT-dG$^{FPA}$ nucleoside

LCAA-CPG solid support (2 g) was mixed with succinic anhydride (1 g) and N-methylimidazole (850 µl) in dry pyridine (10 ml) and shaken at room temperature for 10–15 hours. After filtration, the support was washed with aqueous pyridine (3×5 ml), dry pyridine (3×5 ml) and diethyl ether (2×5 ml) and dried under vacuum.

The attachment of DMT-dG$^{BPA}$ or DMT-dG$^{FPA}$ was carried out by suspending succinylated LCAA-CPG solid support (300 mg) in dry pyridine (3 ml) containing either DMT-dG$^{BPA}$ nucleoside (359 mg, 0.468 mmole) or DMT-dG$^{FPA}$ nucleoside (330 mg, 0.468 mmole), dimethylaminopyridine (45 mg. 0.369 mmole) and DCC (360 mg, 1.71 mmole) and shaken at room temperature for 48 hours. After 48 hours, p-nitrophenol (270 mg, 1.98 mmol) was added and the agitation continued for 20 hours. The reaction was quenched by the addition of morpholine (150 µl) and the shaking was continued for another 2 hours. This step is necessary to cap unreacted carboxylic acid groups. The CPG was filtered, washed with methanol and ether and finally dried under vacuum.

A further DMT assay showed a nucleoside loading of 29.94 µmole/gm for DMT-dG$^{FPA}$-CPG and 33.32 µmole/gm for DMT-dG$^{BPA}$-CPG.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A compound of general formula I

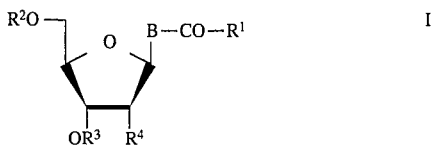

wherein $R^1$ represents —CR'R"—Ar, in which Ar is selected from the group consisting of mono- and dihalo- substituted phenyl, and methoxy phenyl, and R' and R" are independently selected from the group consisting of hydrogen and lower alkyl; one of $R^2$ and $R^3$ is a hydroxyl-protecting group and the other is selected from the group consisting of phosphoramidites, phosphonates, and groups suitable for attachment of the nucleoside to a solid support; $R^4$ is selected from the group consisting of hydrogen, —OH and protected hydroxyl; and B represents a divalent radical corresponding to a purine or pyrimidine base and wherein —CO—$R^1$ is attached to an exocyclic N of B.

2. A compound according to claim 1, wherein B is selected from the group consisting of

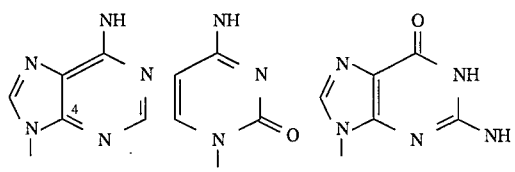

and wherein —CO—$R^1$ is attached to the exocyclic base N.

3. A compound according to claim 1, wherein the hydroxyl-protecting group is selected from the group consisting of 4,4'-dimethoxytrityl, 4,4',4"-tris-(benzyloxy)trityl, 4,4',4"-tris-(4,5-dichlorophthalimido)trityl, 4,4',4"-tris(levulinyloxy)trityl, 3-(imidazolylmethyl)-4,4'-dimethoxytrityl, pixyl (9-phenylxanthen-9-yl), 9-(p-methoxyphenyl)xanthen-9-yl, 4-decyloxytrityl, 4-hexadecyloxytrityl, 9-(4-octadecyloxyphenyl)xanthene-9-yl, 1,1-bis-(4-methoxyphenyl)-1'-pyrenyl methyl, p-phenylazophenyloxycarbonyl, 9-fluorenylmethoxycarbonyl, 2,4-dinitrophenylethoxycarbonyl, 4-(methylthiomethoxy)butyryl, 2-(methylthiomethoxymethyl)-benzoyl, 2-(isopropylthiomethoxymethyl)benzoyl, 2-(2,4-dinitrobenzenesulphenyloxymethyl)benzoyl and levulinyl groups.

4. A compound according to claim 1, wherein the radical suitable for attachment to a solid support is selected from the group consisting of succinate and oxalyl groups.

5. A compound according to claim 1, wherein one of $R^2$ and $R^3$ is selected from the group consisting of 4,4'-dimethoxytrityl, pixyl and levulinyl and the other is a phosphoramidite or phosphonate group.

6. A compound according to claim 5, wherein the phosphoramidite group is a (N,N-diisopropyl)-β-cyanoethylphosphoramidite group.

7. A compound according to claim 1, wherein Ar is selected from the group consisting of mono- and dihalo-substituted phenyl.

8. A compound according to claim 1, wherein R' and R" are both hydrogen.

9. In a method of synthesizing oligonucleotides by a condensation method, the improvement which comprises:

using as a starting material at least one nucleotide derivative of general formula I

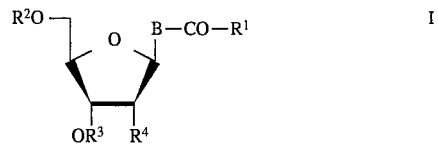

where in $R^1$ represents CR'R"—Ar, in which Ar is selected from the group consisting of mono- and dihalo- substituted phenyl, and methoxy phenyl and R' and R" are independently selected from the group consisting of hydrogen and lower alkyl; one of $R^2$ and $R^3$ is a hydroxyl-protecting group and the other is selected from the group consisting of phosphoramidites, phosphonates, and groups suitable for attachment of the nucleotide to a solid support; $R^4$ is selected from the group consisting of hydrogen, —OH and protected hydroxyl; and B represents a divalent radical corresponding to a purine or pyrimidine base and wherein —CO—$R^1$ is attached to an exocyclic N of B.

10. A method according to claim 9, further comprising deprotecting the oligonucleotide using a reagent selected from the group consisting of agents which are at least 5 times more nucleophilic than ammonia, agents which are at least 1.5 times less polar than water, aqueous ammonia and mixtures thereof.

11. The method according to claim 9, wherein B is selected from the group consisting of

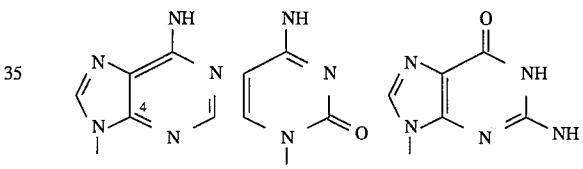

and wherein —CO—$R^1$ is attached to the exocyclic base N.

12. A method according to claim 9, wherein the hydroxyl-protecting group is selected from the group consisting of 4,4'-dimethoxytrityl, 4,4',4"-tris-(benzyloxy)trityl, 4,4',4"-tris-(4,5-dichlorophthalimido)trityl, 4,4',4"-tris(levulinyloxy)trityl, 3-(imidazolylmethyl)-4,4'-dimethoxytrityl, pixyl (9-phenylxanthen-9-yl), 9-(p-methoxyphenyl)xanthen-9-yl, 4-decyloxytrityl, 4-hexadecyloxytrityl, 9-(4-octadecyloxyphenyl)xanthene-9-yl, 1,1-bis-(4-methoxyphenyl)-1'-pyrenyl methyl, p-phenylazophenyloxycarbonyl, 9-fluorenylmethoxycarbonyl, 2,4-dinitrophenylethoxycarbonyl, 4-(methylthiomethoxy)butyryl, 2-(methylthiomethoxymethyl)-benzoyl, 2-(isopropylthiomethoxymethyl)benzoyl, 2-(2,4-dinitrobenzenesulphenyloxymethyl)benzoyl and levulinyl.

13. A method according to claim 9, wherein the radical suitable for attachment to a solid support is selected from the group consisting of succinate and oxalyl groups.

14. A method according to claim 9, wherein one of $R^2$ and $R^3$ is selected from the group consisting of 4,4'-dimethoxytrityl, pixyl and levulinyl and the other is a phosphoramidite or phosphonate group.

15. A method according to claim 14, wherein the phosphoramidite group is a (N,N-diisopropyl)-β-cyanoethylphosphoramidite group.

16. A method according to claim 9, wherein Ar is selected from the group consisting of mono- and dihalo- substituted phenyl.

17. A method according to claim 9, wherein R' and R" are both hydrogen.

18. A compound of general formula I

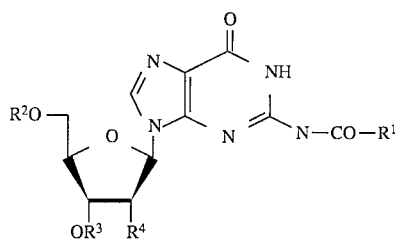

wherein $R^1$ represents —$CH_2$—Ar, in which Ar is selected from the group consisting of mono- and dihalo- substituted phenyl, and methoxyphenyl; one of $R^2$ and $R^3$ is a hydroxyl-protecting group and the other is selected from the group consisting of phosphoramidites, phosphonates, and groups suitable for attachment of the nucleoside to a solid support; and $R^4$ is selected from the group consisting of hydrogen, —OH, and protected hydroxyl.

19. The compound of claim 18 wherein groups suitable for attachment of the nucleoside to a solid support are selected from the group consisting of succinate and oxalyl.

20. The compound of claim 18 wherein protected hydroxyl is selected from the group consisting of 4,4'-dimethoxytrityl, pixyl and levulinyl.

* * * * *